United States Patent [19]
Baldwin et al.

[11] Patent Number: 5,403,846
[45] Date of Patent: Apr. 4, 1995

[54] SPIROCYCLES
[75] Inventors: John J. Baldwin, Gwynedd Valley; David A. Claremon, Maple Glen; Gerald S. Ponticello, Lansdale; Harold G. Selnick, Ambler, all of Pa.
[73] Assignee: Merck & Co., Inc., Rahway, N.J.
[21] Appl. No.: 155,668
[22] Filed: Nov. 22, 1993
[51] Int. Cl.$^6$ .................. A61K 31/44; C07D 211/00; C07D 311/96
[52] U.S. Cl. .................. 514/278; 514/456; 546/15; 549/15; 549/23; 549/336; 549/345; 549/331
[58] Field of Search .................. 546/15; 549/331, 23, 549/336, 345, 15; 514/278, 456
[56] References Cited

U.S. PATENT DOCUMENTS

| | | | |
|---|---|---|---|
| 3,649,635 | 3/1972 | Von Strandtmann et al. | 546/15 |
| 3,686,186 | 8/1972 | Houlihan et al. | 546/15 |
| 3,980,655 | 9/1976 | Kunstmann et al. | 424/250 |
| 4,166,119 | 8/1979 | Effland et al. | 546/217 |
| 4,353,900 | 10/1982 | Clark | 544/71 |
| 4,420,485 | 12/1983 | Davis et al. | 546/17 |
| 4,544,654 | 10/1985 | Davey et al. | 514/210 |
| 4,629,739 | 12/1986 | Davey et al. | 514/605 |
| 4,650,798 | 3/1987 | Minami et al. | 514/227 |
| 4,788,196 | 11/1988 | Cross et al. | 514/252 |
| 4,797,401 | 1/1989 | Kemp et al. | 514/255 |
| 4,804,662 | 2/1989 | Nickisch et al. | 514/252 |
| 4,806,536 | 2/1989 | Cross et al. | 514/252 |
| 4,806,555 | 2/1989 | Lunsford | 514/652 |
| 4,810,792 | 3/1989 | Kosley, Jr. | 546/207 |
| 4,845,099 | 4/1989 | Ruger et al. | 514/253 |
| 5,206,240 | 4/1993 | Baldwin et al. | 514/253 |

FOREIGN PATENT DOCUMENTS

| | | |
|---|---|---|
| 0121972 | 10/1984 | European Pat. Off. . |
| 0235752 | 9/1987 | European Pat. Off. . |
| 0281254 | 9/1988 | European Pat. Off. . |
| 0284384 | 9/1988 | European Pat. Off. . |
| 0285284 | 10/1988 | European Pat. Off. . |
| 0285323 | 10/1988 | European Pat. Off. . |
| 0286277 | 10/1988 | European Pat. Off. . |
| 0286278 | 10/1988 | European Pat. Off. . |
| 0300908 | 1/1989 | European Pat. Off. . |
| 0307121 | 3/1989 | European Pat. Off. . |
| 0397121 | 11/1990 | European Pat. Off. . |
| 63-63533 | 12/1988 | Japan . |

OTHER PUBLICATIONS

Cai et al. Chem. Abst. 119(19):202727d (1993).
Harada et al, Chem. Abst. 115(7):71398q (1991).
Kabbe, Chem. Abst. 94(19):156753z (1980).
Kabbe, Chem. Abst. 91(3):15181n (1979).
Kabbe, Chem. Abst. 88(1):6722a (1977).
Kabbe, Chem Abst. 86(25):189716c (1977).
Bauer, et al., J. Med. Chem., 19, (1976) p. 1315–1324.
Iorio, et al., II Farmaco-Ed Sci., 32, (1977) pp. 212–219.
Parham, et al., J. Org. Chem., 41, (1976) pp. 2628–2633.

Primary Examiner—Cecilia Tsang
Attorney, Agent, or Firm—Francis P.; Mark R. Daniel; Joseph F. DiPrima

[57] ABSTRACT

Compounds of the general formula:

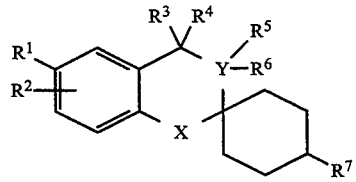

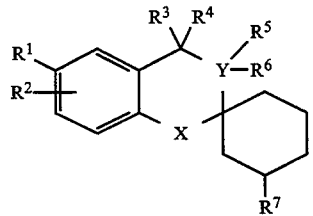

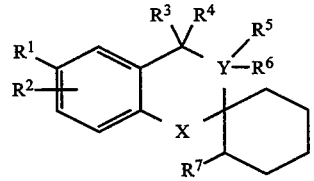

or a pharmaceutically acceptable salt, hydrate or crystal form enantiomer, diastereomer or mixtures thereof are Class III antiarrhythmic agents.

11 Claims, No Drawings

SPIROCYCLES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety, have not been obtained. For example, antiarrythmic agents of Class I according to the classification of Vaughan-Williams which cause a selective inhibition of the maximum velocity of the upstroke of the action potential ($V_{max}$) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:

(1) EP 397,121-A, (2) EP 300,908-A, (3) EP 307,121,
(4) U.S. Pat. No. 4,629,739, (5) U.S. Pat. No. 4,544,654, (6) U.S. Pat. No. 4,788,196,
(7) EP application 88302597.5,
(8) EP application 88302598.3,
(9) EP application 88302270.9,
(10) EP application 88302600.7,
(11) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; J. Med. Chem., 19, 1315 (1976) by Bauer et al; Iorio et al in Il. Farmaco-Ed Sci., 32, 212-219 (1977); Houlihan et al, U.S. Pat. No. 3,686,186; Davis et al, U.S. Pat. No. 4,420,485; Kealey, U.S. Pat. No. 4,810,792; Parham et al, J. Org. Chem., 41, 2629 (1976). None of the compounds disclosed in the foregoing references are alleged to have antiarrhythmic activity.

Now with the present invention, there is provided as antiarrhythmic agents new compounds with an increased degree of activity.

SUMMARY OF THE INVENTION

This invention is concerned with novel spirocycles of general structural formula:

Compounds of the general structural formula:

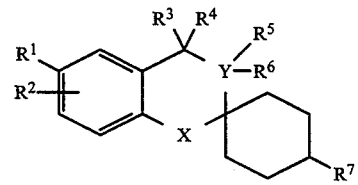

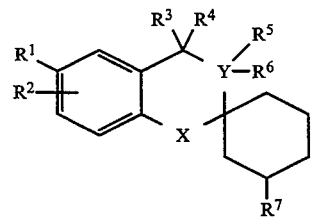

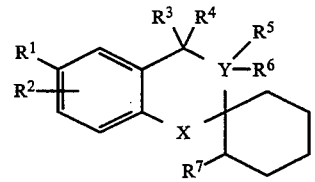

or a pharmaceutically acceptable salt, hydrate, crystal form, enantiomer, diastereomer or mixtures thereof, wherein;

X is O, S, or $CH_2$;
Y is C or O; with the proviso that,
If Y is O, then $R^5$ and $R^6$ are absent and X is $CH_2$;
If X is O or S, then Y is C;
$R^1$ is $H_3CSO_2NH-$, $H_3CO-$, $AlkylSO_2-$, $AlkylCONH-$ or $NO_2-$;
$R^2$ is $-H$, $-OCH_3$ or Alkyl;
$R^3$ and $R^4$ taken together are =O, or $R^3$ is H and $R^4$ is H, $-OH$, $-NHCOCH_3$, $-NHCOCH_3SO_2Phenyl$, $-NHCOCH_3SO_2Alkyl$, $NHCOCH_2SPhenyl$, $NHCOCH_2SAlkyl$, $-NHCOC(CH_3)_2OH$ or $NHSO_2Alkyl$;
$R^5$ and $R^6$ are independently H, $C_1$-$C_6$ Alkyl, or when taken together are
$-(CH_2)n-$, where n is 2-5; or $=CH_2$ $R^7$ is

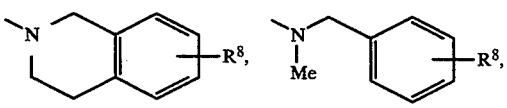

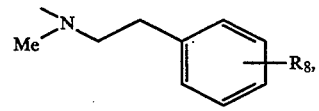

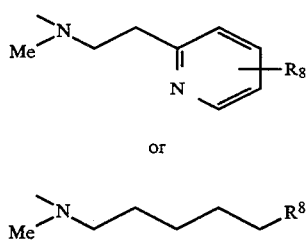

or

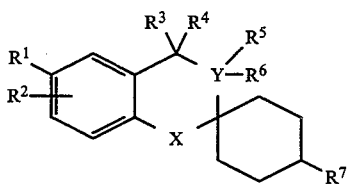

And

R8 is —H —CH₃, —OH, —CN, —O—C1—C6—alkyl, —NHCOAlkyl, —NHSO₂Alkyl, or —SO₂Alkyl; are Class III antiarrhythmic agents.

The invention is also concerned with pharmaceutical formulations comprising one or more of the novel compounds as active ingredient, either alone or in combination with one or more of a Class I, Class II or Class IV antiarrhythmic agent.

The invention is also concerned with a method of treatment of arrhythmia and impaired cardiac pump functions with the above-described novel compounds and formulations thereof.

The invention is further concerned with processes for preparing the novel compounds.

DETAILED DESCRIPTION OF THE INVENTION

Spirocycles of general structural formula:
Compounds of the general structural formula:

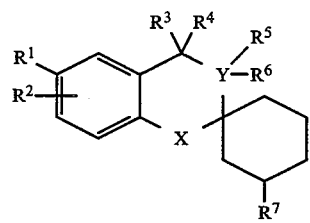

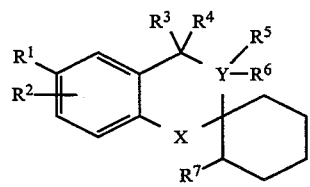

or a pharmaceutically acceptable salt, hydrate, crystal form, enantiomer, diastereomer or mixtures thereof, wherein;

or a pharmaceutically acceptable salt, hydrate, crystal form, enantiomer, diastereomer or mixtures thereof, wherein;

X is O, S, or CH₂;

Y is C or O; with the proviso that,

If Y is O, then R⁵ and R⁶ are absent and X is CH₂;

If X is O or S, then Y is C;

R¹ is H₃CSO₂NH—, H₃CO—, AlkylSO₂—, AlkylCONH— or NO₂—;

R² is —H, —OCH₃ or Alkyl;

R³ and R⁴ taken together are=O, or R³ is H and R⁴ is H, —OH,

—NHCOCH₃, —NHCOCH₃SO₂Phenyl, —NHCOCH₃SO₂Alkyl,

NHCOCH₂SPhenyl, NHCOCH₂SAlkyl, —NHCOC(CH₃)₂OH or

NHSO₂Alkyl;

R⁵ and R⁶ are independently H, C₁-C₆ Alkyl, or when taken together are —(CH₂)n—,where n is 2-5; or=CH₂

R⁷ is

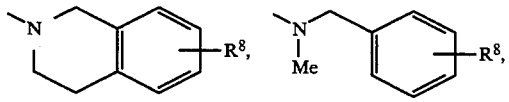

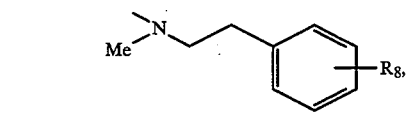

or

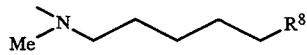

And R8 is —H —CH₃, —OH, —CN, —O—C1-C6—alkyl, —NHCOAlkyl, —NHSO₂Alkyl, or —SO₂Alkyl; are Class III antiarrhythmic agents.

Preferred compounds include:

N-[4'-(3,4-dihydro-2(1H)-isoquinolinyl)-3,4-dihydro-4-oxospiro[2H-1-benzopyran-2,1'-cyclohexan]-6-yl]methanesulfonamide alpha and beta isomers

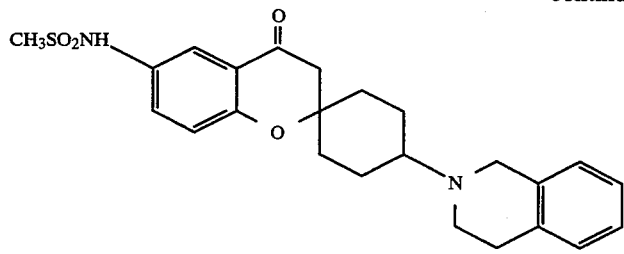

N-[4'-(3,4-dihydro-2(1H)-isoquinolinyl)-3,4-dihydro-4-hydroxyspiro[2H-1-benzopyran-2,1'-cyclohexan]-6-yl]methanesulfonamide alpha and beta isomers N-[4'-(3,4-dihydro-2(1H)-isoquinolinyl)-3,4-dihydrospiro[2H-1-benzopyran-2,1'-cyclohexan]-6-yl]methanesulfonamide beta isomer

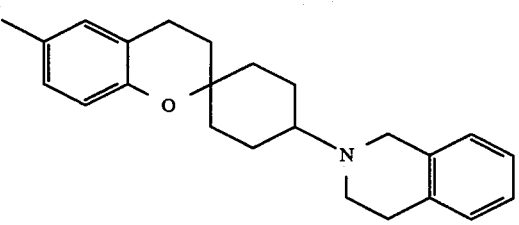

N-[4'-(3,4-dihydro-2(1H)-isoquinolinyl)-3-methyl-3,4-dihydrospiro[2H-1-benzopyran-2,1'-cyclohexan]-6-yl]methanesulfonamide alpha and beta isomers

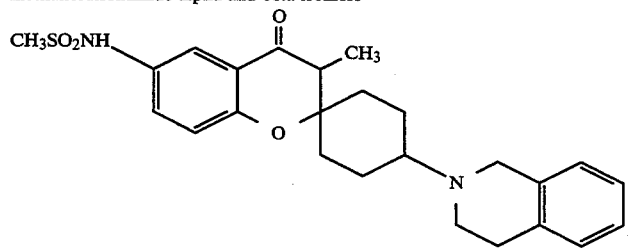

N-[4'-(6-cyano-3,4-dihydro-2(1H)-isoquinolinyl)-3,4-dihydro-4-oxospiro[2H-1-benzopyran-2,1'-cyclohexan]-6-yl]methanesulfonamide alpha and beta isomers

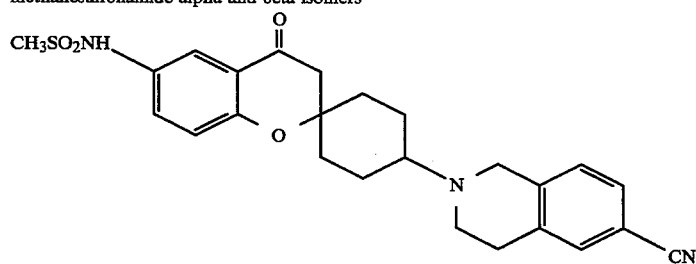

N-[4'-(6-cyano-3,4-dihydro-2(1H)-isoquinolinyl)-3,4-dihydro-4-hydroxyspiro[2H-1-benzopyran-2,1'-cyclohexan]-6-yl]methanesulfonamide beta isomer

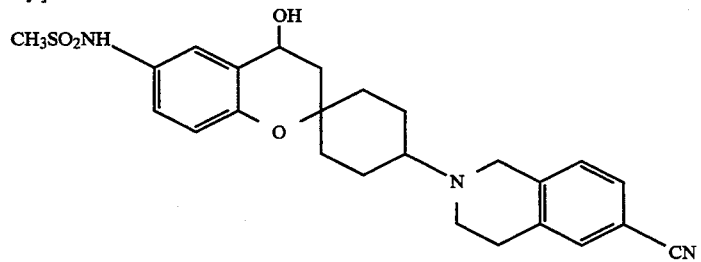

N-[4'-(3,4-dihydro-2(1H)-isoquinolinyl)-3,4-dihydro-4-acetamidospiro[2H-1-benzopyran-2,1'-cyclohexan]-6-yl]methanesulfonamide beta isomer -continued

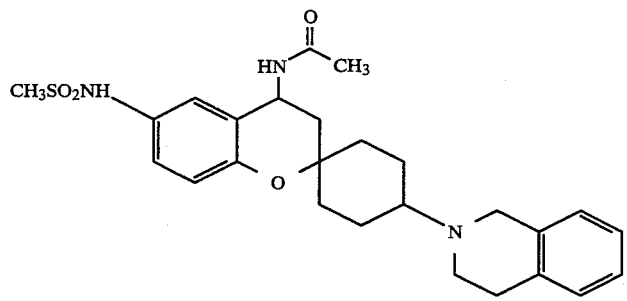

N-[N'-Methyl-N'(p-cyanobenzyl)-4'-amino-3,4-dihydro-4-
oxospiro[2H-1-benzopyran-2,1'-cyclohexan]-6-yl]
methanesulfonamide alpha and beta isomers

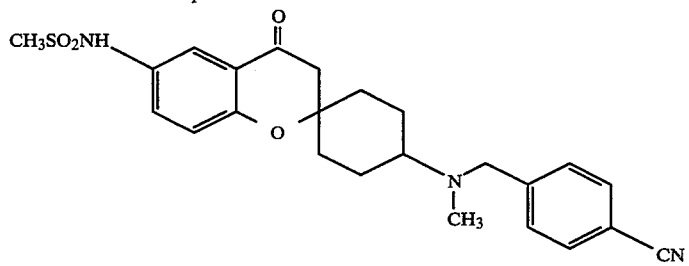

N'-Methyl-N'-benzyl-4'-amino-3,4-dihydro-4-oxospiro[2H-1-
benzopyran-2,1'-cyclohexan]-6-yl]methanesulfonamide alpha
and beta isomer

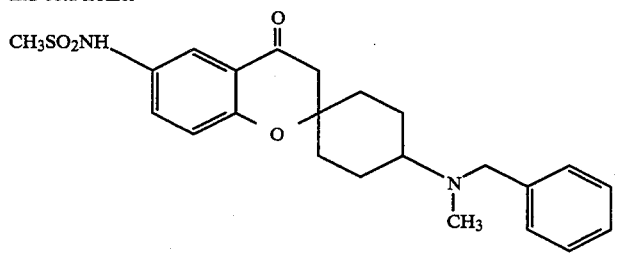

N'-Methyl-N'-phenethyl-4'-amino-3,4-dihydro-4-oxospiro-
[2H-1-benzopyran-2,1'-cyclohexan]-6-yl]methanesulfonamide
alpha and beta isomers

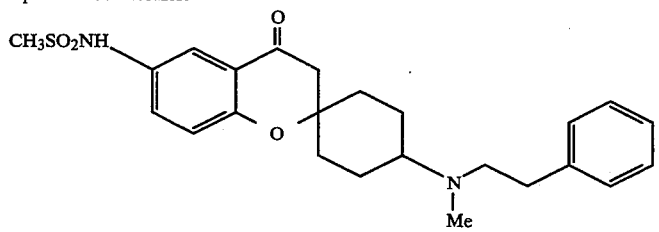

N'-Methyl-N'-p-cyanobenzyl-4'-amino-3,4-dihydro-6-
methoxy-4-oxospiro[2H-1-benzopyran-2,1'-cyclohexane beta
isomer

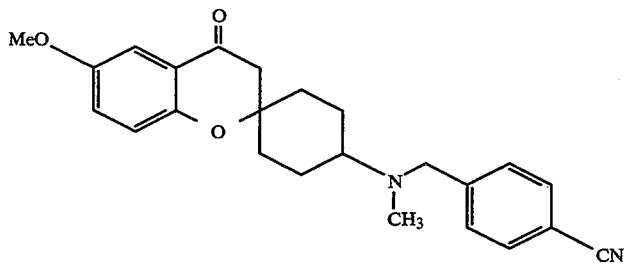

N'-Methyl-N'-benzyl-4'-amino-3,4-dihydro-6-methoxy-4-
oxospiro[2H-1-benzopyran-2,1'-cyclohexane alpha and beta
isomers

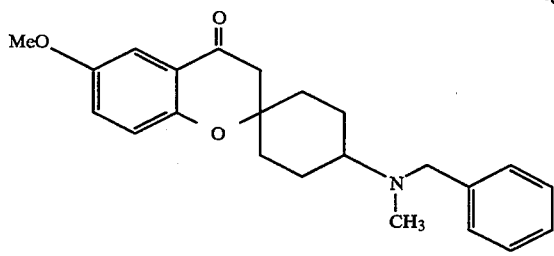

N'-Methyl-N'-phenethyl-4'-amino-3,4-dihydro-6-methoxy-4-oxospiro[2H-1-benzopyran-2,1'-cyclohexane alpha and beta isomers

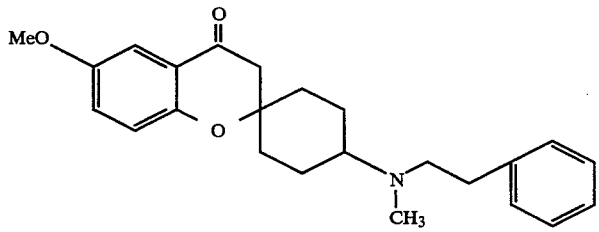

N-[N'-Methyl-N'(p-cyanobenzyl)-4'-amino-3,4-dihydro-4-hydroxyspiro[2H-1-benzopyran-2,1'-cyclohexan]-6-yl]methanesulfonamide beta isomer

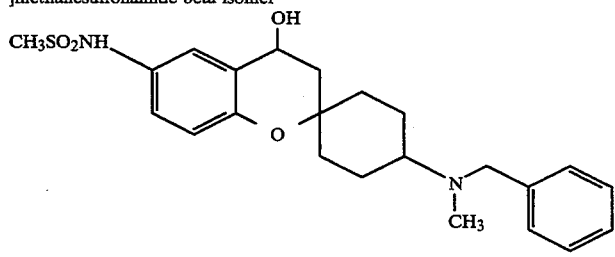

N-[N'-Methyl-N'(p-cyanobenzyl)-4'-amino-3,4-dihydro-4-acetamidospiro[2H-1-benzopyran-2,1'-cyclohexan]-6-yl]methanesulfonamide beta isomer

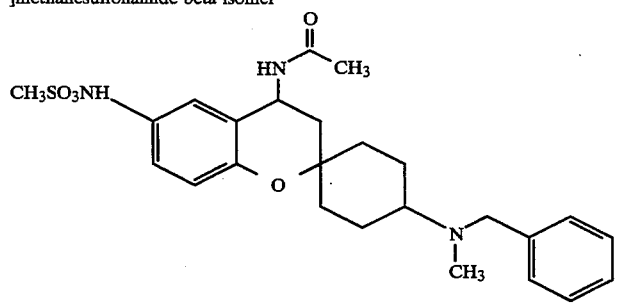

and pharmaceutically acceptable salts, hydrates and crystal forms thereof.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, methanesulfonic acid, isethionic acid, succinic acid, acetic acid, citric acid, tartaric acid, phosphoric acid, or the like. Also included within the scope of this invention are N-oxides.

Also included within the scope of this invention are diastereomers and enantiomers of the novel compounds and mixtures thereof.

The novel compounds of the present invention, have the pharmacological properties required for the antiarrhythmic agents of Class III, namely the prolongation of the myocardial action potential in vitro, without a significant depression of the $V_{max}$, and the prolongation of $QT_c$-interval in anesthetized dogs.

In addition these compounds also have the pharmacological properties required for the antiarrhythmic agents of Class III. Moreover, the members of both groups of compounds in general are much more potent than the reference drug, sotalol.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents, such as a Class I, Class II or Class IV antiarrhythmic agent.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocaninide, flecainide and propafenone. By Class II antiarrhythmic compounds is meant those agents which block sympathetic activity.1 Exemplary of this class of compounds are propranolol and acebutolol. By Class III antiarrhythmic agents is meant those compounds which prolong the effective refractory period without altering the resting membrane potential or rate of depolarization. In addition to the novel comounds of this invention, compounds such as amiodarone, bretylium and sotalol are considered to be in this class. Class IV antiarrhythmic agents are effective in clacium channel blockade.

These compounds, or pharmaceutically acceptable salts thereof, in the described dosages, are administered orally, intraperitoneally, subcutaneously, intramuscularly, transdermally, sublingually or intravenously. They are preferrably administered intravenously or orally, for example in the form of tablets, troches, capsules, elixirs, suspensions, syrups, wafers, chewing gum, controlled release delivery systems or the like prepared by art recognized procedures. The amount of active compound in such therapeutically useful compositions or preparations is such that a suitable dosage will be obtained.

EXAMPLES

The following examples are given for the purpose of illustrating the present invention and shall not be construed as being limitations on the scope or spirit of the instant invention. The terms alpha and beta refer to the difference in chromatographic mobility of the isomers. The alpha isomer is always the less polar of the two.

The novel processes of this invention can be exemplified by the following Reaction Schemes:

SCHEME I

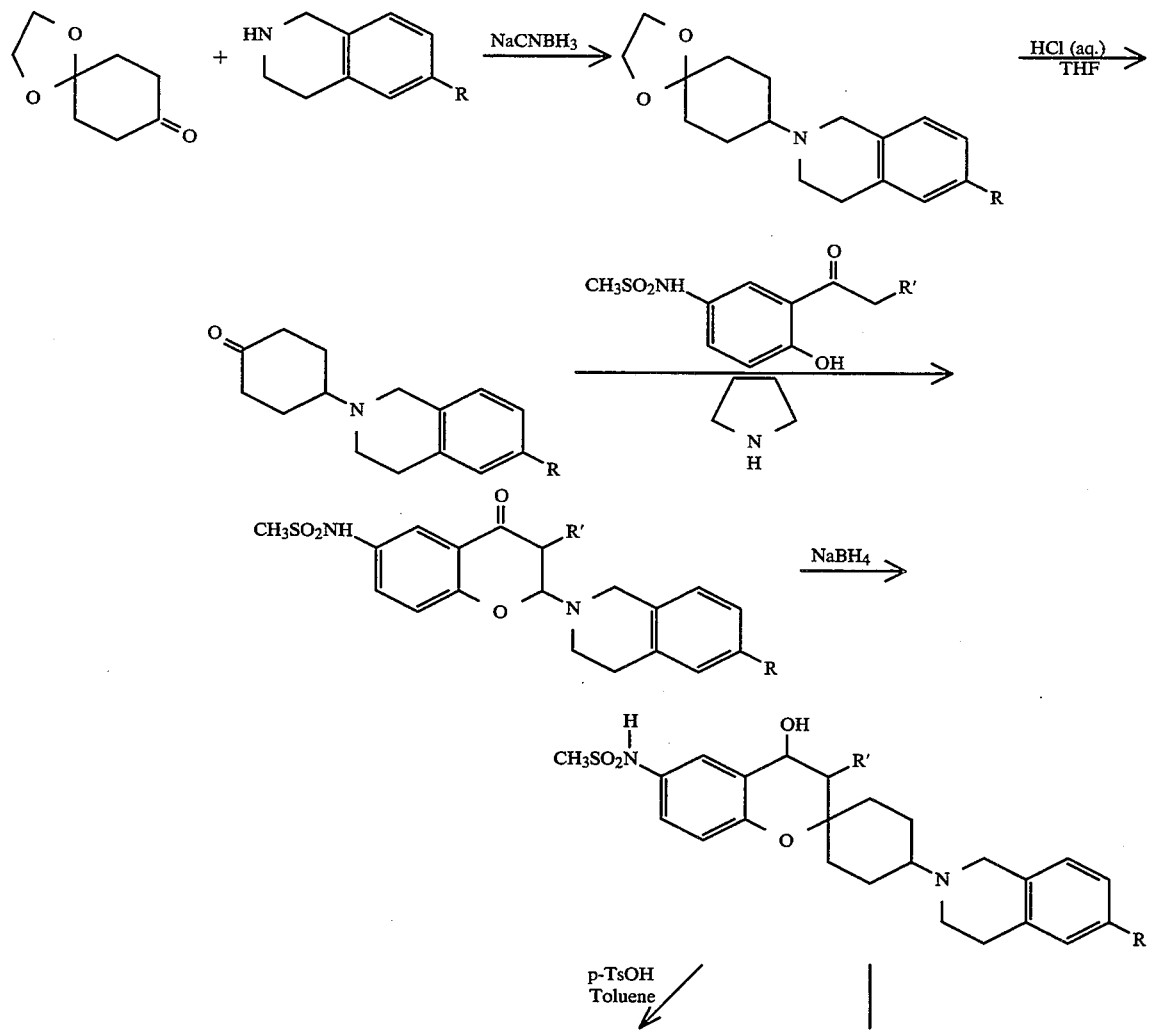

13    5,403,846    14
-continued
SCHEME I
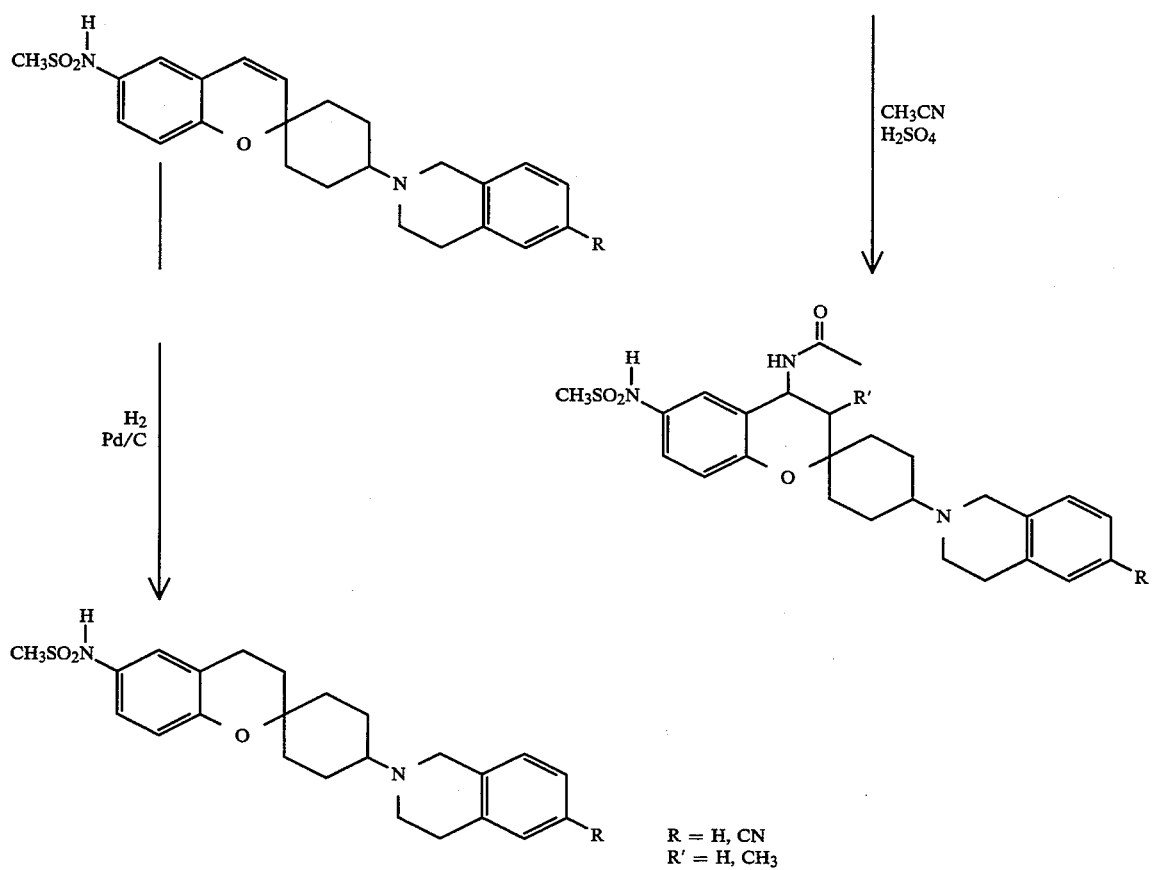
R = H, CN
R' = H, CH₃
SCHEME 2
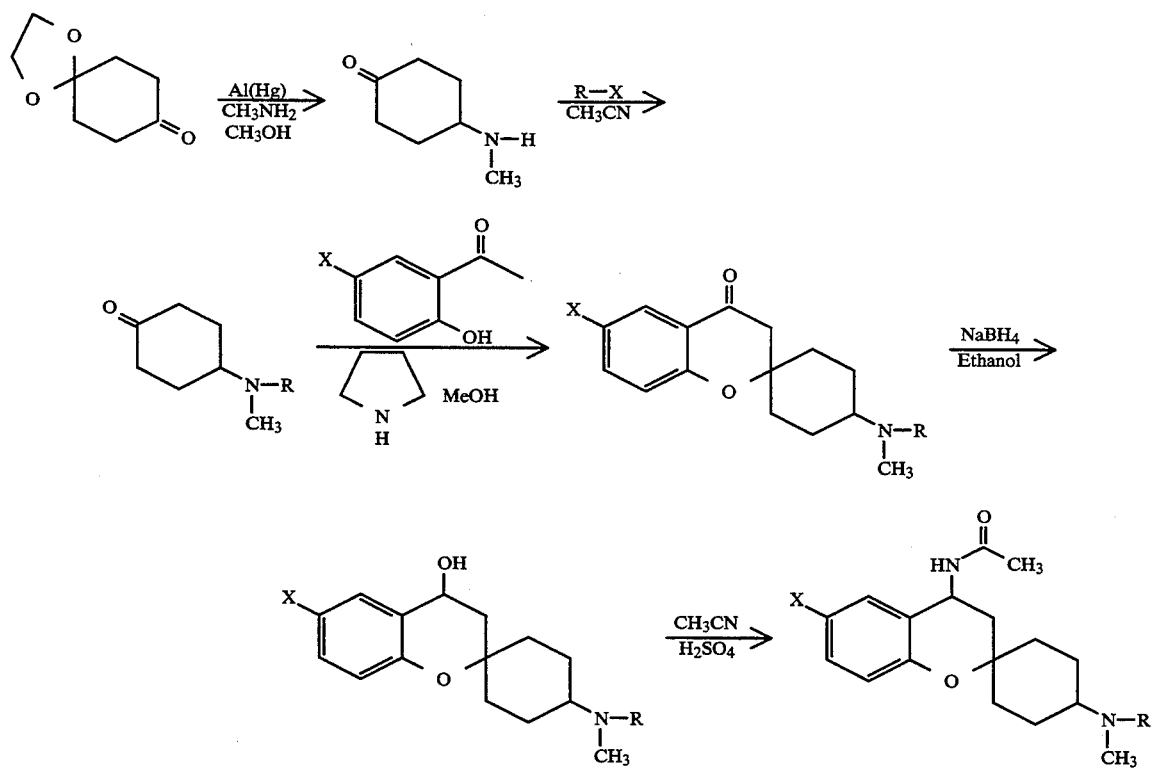

-continued
SCHEME 2

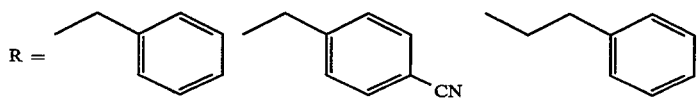

X = MeO—, MeSO₂NH—

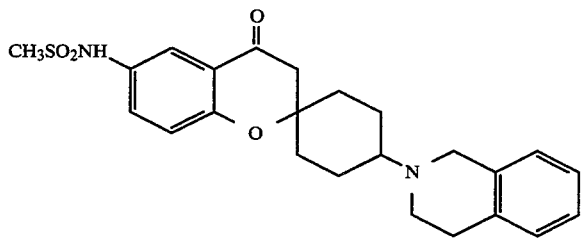

EXAMPLE 1

N-[4'-(3,4-dihydro-2(1H)-isoquinolinyl)-3,4-dihydro-4-oxospiro[2H-1-benzopyran-2,1'-cyclohexan]-6-yl]methanesulfonamide Step A: Prep of 8-(Tetrahydroisoquinolin-2-yl )-1,4-dioxaspiro[4,5]decane A solution of tetrahydroisoquinoline (13.3 g ,100 mmol) and 1,4-cyclohexanedionemonoethylene ketal(15.6 g, 100 mmol) in toluene (1 L) was treated with p-tolunesulfonic acid (100 mg) and heated to reflux in the presence of a Dean-Stark trap to remove water. After 3 hr the solution was cooled and concentrated in vacuo. the residue was dissolved in THF (1L) and HCL gas was introduced until the pH was between 2 and 3. Sodium cyanoborohydride was added and the reaction stirred over night at room temperature. The reaction was concentrated to ¼ volume at reduced pressure and poured into sat. NaHCO₃ (500 ml ) and extracted with EtOAc (3×500 ml ). The combined organic layers were dried over anhydrous MgSO4 and evaporated under reduced pressure. The resulting foam was chromatographed on silica gel, eluting with 50% ethyl acetate/-hexane to .give 10.3 of product as a viscous oil. ¹H NMR CDCl₃δ7.1–6.9 (m, 4H), 3.95 (s, 4H), 3.80 (s, 2H), 2.95–2.80 (m, 4H), 2.65–2.55 (m, 1H), 1.95–1.50 (m, 8H)

Step B: Prep of 4-(Tetrahydroisoquinolin-2yl)cyclohexanone.

A solution of the product of step A above in THF (100 mL) was treated with a solution of 1N HCL (120 mL) and heated to reflux for 2 hr. The solution was cooled to room temperature and poured into 400 mL water and neutralized with 150 mL of 1N NaOH. The cloudy mixture was extracted with ether (3×400 mL) the ether layers were dried over MgSO4, filtered and concentrated at reduced pressure to give 8.1 g of the product as a viscous oil. ¹H NMR CDCl₃δ7.1–6.9 (m, 4H), 3.80 (s, 2H), 2.95–2.80 (m, 5H), 2.65–2.50 (m, 2H), 2.40–2.35 (m, 2H), 2.20–2.05 (m, 2H), 2.05–1.90 (m, 2H).

Step C: Preparation of N-[4'-(3,4-dihydro-2(1H)-isoquinolinyl)-3,4-dihydro-4-hydroxyspiro[2H- 1-benzopyran-2,1 '-cyclohexan]-6-yl]methanesulfonamide A solution of 5-methanesulfonamido -2-hydroxyacetophenone (0.50 g, 2.05 mmol) and 4-(Tetrahydroisoquinolin-2-yl)cyclohexanone.(0.47 g, 2.05 mmol) were mixed in methanol (5 ml) under argon with pyrrolidine (0.15 g, 2.05 mmol) and stirred at room temperature for 18 h. The products were chromatographed on silica gel with a 50:50 to 90:10 ethyl acetate:hexane gradient elution, yielding two isomers, α and β. The hydrochloride salts of each isomer were prepared in ethanol.

For α isomer, MP=280°–285° ; Analysis Calculated for C₂₄H₂₈N₀₄S.HCl:.0.03 EtOH C, 60.40; H, 6.15; N, 5.86. Found: C, 60.06; H, 6.03; N, 6.05.

For the β isomer, Melting point=273°–275° C. w/decomp Calculated for C₂₅H₂₉N₂O₄S.HCl.0.10 EtOH: C, 60.34; H, 6.19; N, 5.82. Found: C, 60.07; H, 6.10; N, 6.05.

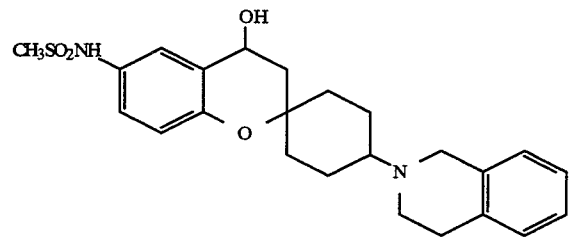

EXAMPLE 2

N-[4'-(3,4-dihydro-2(1H)-isoquinolinyl)-3,4-dihydro-4hydroxyspiro[2H-1-benzopyran-2,1'-cyclohexan]-6-yl]methanesulfonamide To a stirred suspension of the product of Example 1 ( 0.5Sg, 1.1 mmol) in 20 ml. ethanol was added NaBH4 ( 0.042 g, 1.1 mmol). This was stirred under argon at r.t. overnight. Another portion of NaBH₄ (0.042 g, 1.1 mmol) was added the following morning and the reaction appeared to go to completion by TLC. The reaction mixture was diluted with sat. NaHCO₃ ( 20 ml ) and extracted with EtOAc (3×20 ml ). The combined organic layers were dried over Na₂SO₄ and evaporated under reduced pressure. The resulting foam was chromatographed over silica gel, eluting with 10% MeOH:CHCl₃ to give 0.31 g of a white foam, 63.6%. ¹H NMR (CDCl₃)δ7.32 (d, J=3 Hz, 1H), 7.14–7.03 (m, 5H), 6.84 (d, J=9 Hz, 1H ), 4.83–4.78 (m, 1H) 3.81 (s, 2H), 2.94 (s, 2H), 2.91(s, 3H), 2.60–2.53 (m, 1H ), 2.14–1.34 (m, 14H).

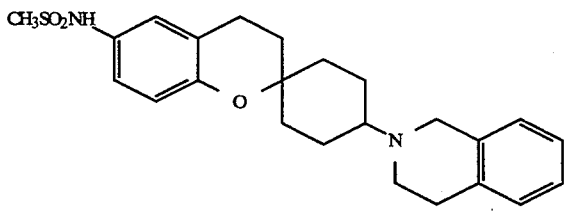

EXAMPLE 3

Preparation of
N-[4'-(3,4-dihydro-2(1H)-isoquinolinyl)-3,4-dihydrospiro[2H-1-benzopyran-2,1'-cyclohexan-]-6-yl]methanesulfonamide Step A: Preparation of N-[4'-(3,4-dihydro-2(1H)-isoquinolinyl)spiro[2H-1-benzopyran-2,1'-cyclohexan]-6-yl]methanesulfonamide To a stirred suspension of the alcohol from example 2 above (310 mg, 0.7 mmol) in toluene (8 ml) was added p-toluene sulfonic acid (200 mg). This was boiled without a condenser until the reaction mixture was a gum. It was then cooled to r.t., sat. NaHCO₃ (1 00 ml) and EtOAc (1 00 ml) were added. The biphasic mixture was stirred at r.t until all of the gummy solid dissolved. The layers were separated and the organic phase was dried over Na₂SO₄ and evaporated under reduced pressure to give 166 mg of a pale yellow oil, 55.8%. $^1$H NMR (CDCl₃)δ7.28–6.79 (m, 7H), 6.30 (d, J=10Hz, 1H), 5.55 (d, J=10 Hz, 1H), 3.83 (s, 2H), 2.91 (s, 7H), 2.62–2.48 (m, 1H), 2.20 (d, J=12 Hz, 2H), 2.00–1.82 (m, 4H), 1.45 (dt, J=13 Hz, J=4 Hz, 2H).

Step B: Preparation of N-[4'-(3,4-dihydro-2(1H)-isoquinolinyl)-3,4-dihydrospiro[2H- 1-benzopyran-2,1'-cyclohexan]-6-yl]methanesulfonamide To a stirred suspension of 5% Pd/C (10 wt. %, 1.7 mg) in ethanol (25 ml) was added the olefin from step A above. The system was evacuated and purged with hydrogen twice and the reaciton mixture stirred at r.t. under 1 atm. of hydrogen. After three hours another portion of Pd/C (20 wt.%, 3.4 mg) was added and the reaction stirred overnight at r.t. It was then filtered through celite, the pad rinsed with ethanol and evaporated under reduced pressure. The resulting oil was chromatographed over silica gel with eluting with 5% MeOH:CHCl₃. The pure material was recrystallized from EtOH to give 100 mg of off white crystals. 60.1%. mp 183°–185 ° C. $^1$H NMR (CDCl3)δ7.11–6.79 (m, 8H), 4.14 (s,2H), 2.93 (s, 5H), 2.91 (s, 2H), 2.76 (t, J=7 Hz, 2H), 2.66–2.54 (m, 1H), 2.00 (d, J=9 Hz, 2H), 1.90–1.72 (m, 6H), 1.46–1.20 (m, 2H) Anal. Calcd for C₂₄H₃₀N₂O₃S.0.15H₂O: C, 67.14; H, 7.11; N, 6.53. Found: C, 67.17; H, 6.99; N, 6.45.

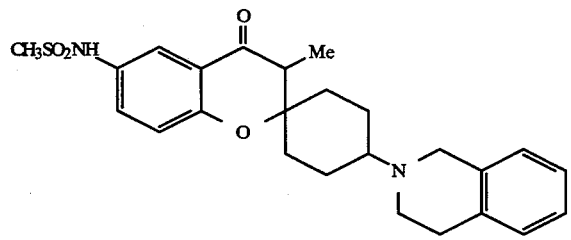

EXAMPLE 4

N-[4'-(3,4-dihydro-2(1H)-isoquinolinyl)-3-methyl-3,4-dihydrospiro[2H-1-benzopyran-2,1'-cyclohexan]-6-yl]methanesulfonamide Step A: Preparation of 5'-Acetamido-2'-hydroxypropiophenone N-(4-methoxyphenyl)acetamide (40.0 g, 0.244 mol) in methylene chloride (100 ml) was mixed with propionyl chloride (65.0 g, 0.702 mol, 61.0 ml) via overhead stirring. Aluminum chloride (100 g, 0.75 mol) was added in portions and the mixture was heated without a condenser at 60° C. until the methylene chloride evaporated to the point where the mixture could no longer be stirred. Methylene chloride was added to facilitate mixing and the mixture was cooled to 0° C. and crushed ice was stirred in to quench the reaction. The yellow-green solid 2 was isolated by filtration and rinsed with water and dried in vacuo in 99% yield. d$_H$ (DMSO-d₆) 11.8 (1H, s), 10.2 (1H, s), 8.3 (1H, d, J=2.6 Hz), 7.88 (1H, dd, J=2.6, 8.8 Hz), 7.15 (1H, d, J=8.8 Hz), 3.28 (2H, q, J=7.2 Hz), 2.26 (3H, s), 1.34 (3H, t, J=7.2 Hz).

Step B: Preparation of 5'-Methanesulfonamido-2'-hydroxypropiophenone

Hydrolysis of the amide to the amine was accomplished by dissolving in 600 ml of ethanol and adding 200 ml of 6N HCl$_{(aq)}$. The dark brown solution was heated to reflux for 12 h. The ethanol and HCl were evaporated and recrystallization was done using ethanol, producing large off-white crystals of. At 0° C., the amine (35.8 g, 0.189 mol) was suspended in methylene chloride (400 ml). Pyridine (35.9 g, 0.454 mol, 36.7 ml) was added, followed by methanesulfonyl chloride (23.8 g, 0.208 mol, 16.1 ml). The mixture was allowed to warm to room temperature after one half hour and stirred for one hour longer. 100 ml of 1N HCl$_{(aq)}$ was added and the acid layer was washed with 2×100 ml portions of methylene chloride. The organic layers were combined, dried with MgSO₄, filtered, and concentrated. The methanesulfonamide was recovered as pink crystals from methylene chloride (75% yield). d$_H$ (DMSO-d₆) 11.6 (1H, s), 9.5 (1H, s), 7.64 (1H ,d, J=3.3 Hz), 7.34 (1H, dd, J=3.3, 3.9 Hz), 6.95 (1H, d, J=8.7 Hz), 3.04 (2H, q, J=7.1 Hz), 2.91 (3H, s), 1.07 (3H, t, J=7.1 Hz).

Step C: Preparation of N-[4'-(3,4-dihydro-2(1H)-isoquinolinyl)-3-methyl-3,4-dihydrospiro[2H- 1-benzopyran-2,1'-cyclohexan]-6-yl]methanesulfonamide The methanesulfonamide from step B above (0.50 g, 2.05 mmol) and 4-(Tetrahydroisoquinolin-2-yl )cyclohexanone from Example 1, step B. (0.47 g, 2.05 mmol) were mixed in isopropanol (5 ml) under argon with pyrrolidine (0.15 g, 2.05 mmol) and heated to reflux for 18 h. The products were chromatographed on silica gel with a 50:50 to 75:25 ethyl acetate:hexane gradient elution, yielding two isomers, α and β. For α isomer, d$_H$ (DMSO-d₆) 9.60 (1H, s), 7.53 (1H, d, J=2.8 Hz), 7.40 (1H, dd, J=9.0,2.8 Hz), 7.1–7.0 (5H, m), 3.64 (2H, s), 3.32 (1H, s), 2.93 (3H, s), 2.85–2.65 (5H, m), 1.98–1.50 (8H, m), 1.03 (3H, d, J=7.1 Hz). Found: C, 65.33; H, 7.04; N, 5.75. Calculated for C₂₅H₂₉NO₄S: C, 65.33; H, 6.86; N, 5.79. Melting point=135° C. w/decomp. For the β isomer, $^1$H (DMSO-d₆) 9.60 (1H, s), 7.54 (1 H, d, J=2.9 Hz), 7.41 (1H, dd, J=8.8, 2.9 Hz), 7.11–7.00 (5H, m), 3.69 (2H, s), 3.32 (1H, s), 2.92 (3H, s), 2.80–2.68 (5H, m),2.02–1.36 (8H, m), 1.06 (3H, d, J=7.1 Hz). Found: C, 61.48; H, 6.17; N, 5.75. Calculated for C₂₅H₂₉N₂O₄S: C,

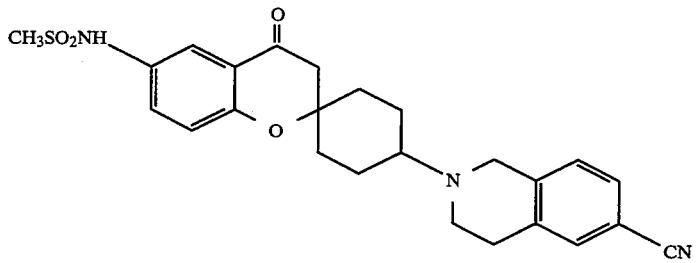

EXAMPLE 5

Preparation of N-[4'-(6-cyano-3,4-dihydro-2 (1H)-isoquinolinyl)-3,4-dihydro-4-oxospiro[2H-1-benzopyran-2,1'-cyclohexan]-6-yl]methanesulfonamide Step A: N-tert-Butoxycarbonyl-6-hydroxy-1,2,3,4-tetrahydroisoquinoline A solution of 6-hydroxy-1,2,3,4-tetrahydroisoquinoline hydrobromide (32 g, 139 mmole) in 200 mL water at room temperature was treated with THF (500 mL) triethylamine (14 g, 139 mmole, 19 mL) and di-tert-butyldicarbonate (30.3 g, 139 mmole). The reaction was stirred at room temperature overnight. The reaction was concentrated at reduced pressure to one third volume and the residue was partitioned between water (500 mL) and ethyl acetate (500 mL). The aqueous phase was extracted with two additional 200 mL portions of ethyl acetate and the combined organics were dried over magnesium sulfate, filtered, and concentrated at reduced pressure. The residue was chromatographed on silica gel using 25% ethyl acetate/hexane as eluent to give 21.2 g (61%) of product as a waxy solid. Mp: 110–112; FABMS (m/e) 250 (M+H); $^1$H NMR CDCl3 δ6.94(1 H, d, J=8 Hz), 6.68(1 H, dd, J=2.4, 8 Hz), 6.63 (1 H, d, J=2.4 Hz), 5.5 (1 H, br s), 4.49 (3H, s), 3.61(2H, t, J=6 Hz), 2.76 (2 H, t, J=6 Hz), 1.49 (9 H, s); Anal. Calcd. For $C_{14}H_{19}NO_3$: C, 67.45; H, 7.68; N, 5.62. Found: C, 67.56; H, 7.78; N, 5.94.

Step B: Preparation of N-tert-butoxycarbony-6-cyano-1,2,3,4-tetrahydro-isoquinoline A solution of N-tert-Butoxycarbonyl-6-hydroxy-1,2,3,4-tetrahydro-isoquinoline (3) (21.2 g, 85 mmole) in methylene chloride(400 mL) at 0° C. was treated with triethylamine(8.6 g, 85 mmole, 11.8 mL) and trifluoromethanesulfonic anhydride(24 g, 85 mmole, 14.3 mL). The reaction was allowed to warm to room temperature and then poured into a solution of saturated sodium bicarbonate. The layers were separated and the aqueous phase extracted with two 200 mL portions of ethyl acetate. The combined organics were dried over magnesium sulfate, filtered, and concentrated at reduced pressure to give 28.8 g of crude triflate. $^1$H NMR CDCl3 δ7.18(1 H, d, J=8 Hz), 7.10 (1 H, dd, J 2.4 Hz), 4.49 (3H, s), 3.66 (2H, t, J=6 Hz), 2.87 (2 H, t, J=6 Hz), 1.49 (9 H, s). The crude triflate (28.8 g, 75.5 mmole) was disolved in DMF (100 mL) and treated with palladium-tetrakistriphenylphosphine (3.5 g, 3 mmole) and Zn(CN)2 (6.2 g, 52.9 mmole, 1.7 eq). The mixture was then heated to 80° C. for 45 minutes. The dark reaction mixture was cooled to room temperature and poured into a solution of saturated sodium bicarbonate. The mixture was extracted with ethyl acetate (3×300 mL) the combined organics were dried over magnesium sulfate, filtered, and concentrated at reduced pressure. The residue was chromatographed on silica gel using 25% ethyl acetate/hexane as eluent to give 13.6 g (69%) of N-tertbutoxycarbony-6-cyano-1,2,3,4-tetrahydro-isoquinoline. Mp: 143–145; FABMS (m/e) 259 (M+H); $^1$H NMR CDCl3 δ7.49–7.42(2 H, m), 7.20 (1 H, d, J=7.8 Hz), 4.62 (3H, s), 3.66(2H, t, J= 5.9 Hz), 2.86 (2 H, t, J=5.9 Hz), 1.49 (9 H, s); Anal. Calcd. For $C_{15}H_{18}N_2O_2$. 0.3 $H_2O$: C, 68.31; H, 7.11; N, 10.62. Found: C, 68.25; H, 6.85; N, 10.87.

Step C: Preparation of 6-cyano-1,2,3,4-tetrahydro-isoquinoline

A solution of N-tert-butoxycarbony-6-cyano-1,2,3,4-tetrahydro-isoquinoline (8.94 g, 34 mmole) in ethyl acetate (500 mL) at room temperature was treated with HCl gas until tlc analysis indicated reaction was complete. The precipitate that formed was collected and dried in vacuo to give 5.86 g (91%) of 6-cyano-1,2,3,4-tetrahydro-isoquinoline(1). MP: 287–289: FABMS (m/e) 150 (M+H); $^1$H NMR d6-DMSO δ9.9 (2 H, br s), 7.75(1 H, br s), 7.68 (1 H, dd, J=1.5, 8.0 Hz), 7.42 (1 H, d, J=8 Hz), 4.30 (3H, s), 3.33(2 H, t, J=5.9 Hz), 3.04(2 H, t, J=5.9Hz); Anal. Calcd. For $C_{10}H_{10}N_2$. HCl: C, 61.70; H, 5.70; N, 14.39. Found: C, 61.36; H, 5.69; N, 14.31.

Step D: Preparation of 8-(6-Cyano-1,2,3,4-tetrahydroisoquinolin-2-yl)- 1,4-dioxaspiro[4,5]decane A solution of cyclohexane-1,4-dione monoethylene ketal(5.3 g, 33.9 mmole) and 6-cyano-1,2,3,4-tetrahydro-isoquinoline (5.3 g, 28.5 mmole) was treated with sodium cyanoborohydride (2.13 g, 33.8 mmole)at room temperature and stirred at ambient temperature for 18 hr. The reaction was concentrated to ¼ volume at reduced pressure and poured into sat. NaHCO3 (500 ml) and extracted with EtOAc (3×500 ml). The combined organic layers were dried over anhydrous MgSO4 and evaporated under reduced pressure. The resulting foam was chromatographed on silica gel, eluting with 50% ethyl acetate/hexane to give 7.01 of product as a white solid which was recrystallized from ethanol. MP=127° C.

Step E: Prep of 4-(6-Cyano-1,2,3,4-tetrahydroisoquinolin-2-yl) cyclohexanone.

A solution of 8-(6-Cyano-1,2,3,4-tetrahydroisoquinolin-2-yl)-1,4,dioxaspiro-[4,5S]decane (7.01 g, 23.4 mmole) (the product of step D above) in THF (30 mL) was treated with a solution of 1N HCL (100 mL) and heated to reflux for 15 minutes. The solution was cooled to room temperature and poured into 300 mL water and neutralized with 110 mL of 1N NaOH. The cloudy mixture was extracted with ethyl acetate (3×200 mL) the ether layers were dried over MgSO4, filtered and concentrated at reduced pressure to give 4.8 g of the product as a viscous oil that solidified on standing. MP=109–110$^1$ H NMR CDCl13 δ δ7.42 (br s, 1 H), 7.40

(br d,j=7.5 Hz, 2H),7.13 (br d,j =7.5 Hz, 2 H),3.85 (s, 2H), 3.00–2.80 (m, 5H), 2.60–2.50 (m, 2H), 2.45–2.35 (m, 2H), 2.20–2.05 (m, 2H), 2.05–1.90 (m, 2H).

Step F: Preparation of N-[4'-(6-cyano-3,4-dihydro-2(1H)isoquinolinyl)-3,4-dihydro-4-oxospiro[2H- 1-benzopyran-2,1 '-cyclohexan]-6-yl]methane-sulfonamide α and β isomers Prepared in a manner similar to that already described for the preparation of example 1, Step C except starting with the product of step E above (4-(6-Cyano-1,2,3,4-tetrahydroisoquinolin-2-yl) cyclohexanone) and 5methanesulfonamido -2-hydroxyacetophenone For α isomer, MP=212°–214° C. w/decomp; Analysis Calcd. for $C_{25}H_{27}N_3O_4S$; C, 64.50 H, 5.85 N, 9.03. Found: C, 64.37; H, 5.61; N, 9.01.

For β isomer, Mp=209°–210° C. w/decomp; Analysis Calcd. for $C_{25}H_{27}N_3O_4S$; C, 64.50 H, 5.85 N, 9.03 Found: C, 64.03 H, 5.73; N, 8.89.

EXAMPLE 7

N-[4'-(3,4-dihydro-2 (1H)-isoquinolinyl)-3,4-dihydro-4-acetamidospiro[2H-1-benzopyran-2,1'-cyclohexan]-6-yl]methanesulfonamide.

A solution of the product of example 2 (1 g, 2.25 mmole) in acetonitrile (150 mL) at room temperature was treated with concentrated sulfuric acid (0.25 mL) and stirred at ambient temperature for one hour. The reaction was poured into sat. $NaHCO_3$ (600 ml ) and extracted with EtOAc (3×250 ml ). The combined organic layers were dried over anhydrous $MgSO_4$ and evaporated under reduced pressure. The resulting foam was chromatographed on silica gel, eluting with 10 % $MeOH/CHCl_3$ to give 0.72 g of product. The hydrochloride salt was generated in ethanol. Mp=250 ° C. Analysis Calcd. for $C_{26}H_{33}N_3O_4S\cdot HCl$. 0.85 $H_2O$: C, 58.24; H, 6.80; N,7.75 Found: C,58.24 ;H, 6.48; N, 7.68.

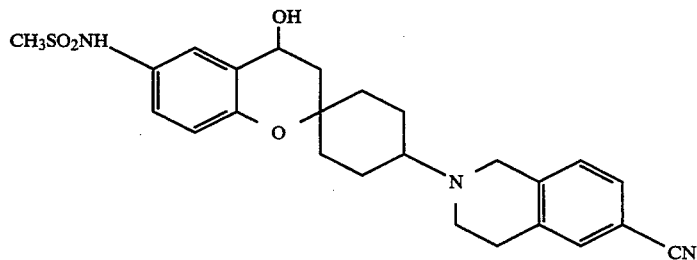

EXAMPLE 6

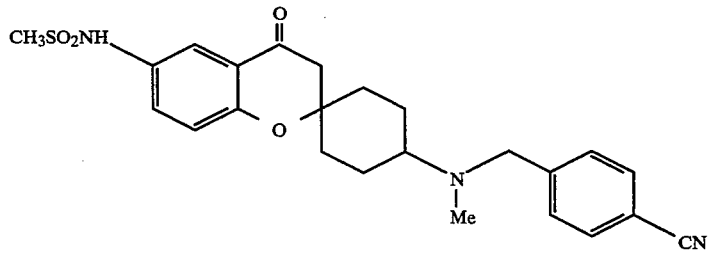

N-[4'-(6-cyano-3,4-dihydro-2 (1H)-isoquinolinyl)-3,4-dihydro-4-hydroxyspiro[2H-1-benzopyran-2,1'-cyclohexan]-6-yl]methanesulfonamide.

Prepared from the beta isomer of Example 5, Step F above by a procedure similar to that already described for the preparation of example 2.

Mp=228°–230° C. w/decomp; Analysis Calcd. for $C_{25}H_{29}N_3O_4S$: C, 64.22 H, 6.25 N, 8.99 Found: C, 63.68 H, 6.25; N, 8.74.

EXAMPLE 8

N-[N'-Methyl-N'(p-cyanobenzyl)-4'-amino-3,4-dihydro-4-oxospiro[2H-1-benzopyran-2,1'-cyclohexan]-6-yl]methanesulfonamide Step A: 8-Methylamino- 1,4-dioxaspirononane A solution of cyclohexanedione monoethylenketal (8 g, 51 mmole) in methanol (800 mL) at room temperature was treated with 25 mL of 40% aqueous methylamine, shredded aluminum foil (20 g) and mercuric

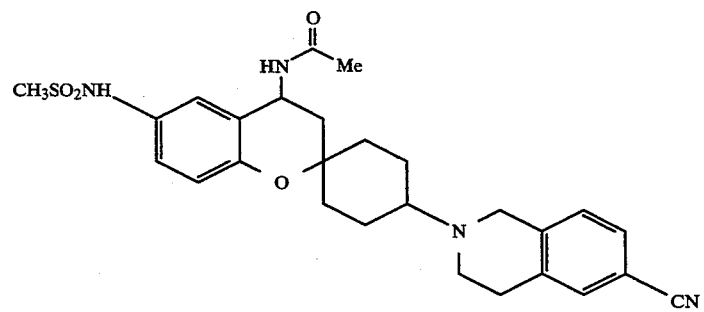

chloride (500 mg). The mixture was stirred with an overhead stirrer for 1 hr. The reaction mixture was filtered thru celite and concentrated at reduced pressure. The residue was dissolved in ethyl acetate and the solid that separated was removed by filtration. The filtrate was then concentrated at reduced pressure to give 7.2 g product as a viscous oil. $^1$H NMR CDCl$_3$δ3.95 (s,4H), 2.42 (s, 3H), 2.42 (m, 1H), 1.95–1.85 (m, 2H), 1.85–1.75 (m, 2H), 1.65–1.50 (m, 2H), 1.50–1.35 (m, 2H), Step B: N-(p-Cyanobenzyl)-8-Methylamino-1,4-dioxaspirononane A solution of the product from step A (8-Methylamino-1,4-dioxaspirononane, 7.2 g, 45.5 mmole) and p-cyanobenzyl bromide (8.92 g, 45.5 mmole) in acetonitrile (100 mL) was heated to reflux for 16 hr. The reaction was cooled to room temperature, poured into sat. NaHCO$_3$ (500 ml) and extracted with EtOAc (3×300 ml). The combined organic layers were dried over anhydrous MgSO4 and evaporated under reduced pressure to give 11.1 g of product. $^1$H NMR CDCl$_3$δ7.60 (d, J=7 Hz, 2H), 7.45 (d, J=7 Hz, 2H), 3.95 (s, 4H), 3.60 (s, 2H), 2.55–2.45 (m, 1H), 2.20 (s, 3H),1.85–1.75 (m,4H), 1.75–1.50 (m,4H)

Step C: N-(p-Cyanobenzyl)-4-Methylamino-cyclohexanone

A solution of the product of step B above (N-(p-Cyanobenzyl)-8-Methylamino-1,4-dioxaspirononane) (11.1 g, 38.76 mmole) in THF (100 mL) was treated with 200 mL of 2N HCl (aq) and heated to 80° C. for 30 minutes. The solution was cooled to room temperature and poured into 400 mL water and neutralized with 70 mL of 6N NaOH. The cloudy mixture was extracted with ethyl acetate (3×300 mL) the organiclayers were dried over MgSO4, filtered and concentrated at reduced pressure to give 8.85 g of the product as a viscous oil. $^1$H NMR CDCl$_3$δ7.65 (d, J=7 Hz, 2H), 7.45 (d, J=7 Hz, 2H), 3.67 (s, 2H), 2.95–2.85 (m, 1H), 2.60–2.45 (m, 2H), 2.40–2.30 (m, 2H), 2.20 (s, 3H),2.20–2.00 (m, 2H), 1.95–1.80 (m, 2H)

Step D: Preparation of N-[N′-Methyl-N′(p-cyanobenzyl)-4′-amino-3,4-dihydro-4-oxospiro[2H- 1-benzopyran-2,1 ′-cyclohexan]-6-yl]methanesulfonamide Prepared from the product of step C above and 5-methanesulfonamido-2-hydroxyacetophenone by a procedure identical to that already described in Example 1, step C. Only the Beta (major and more active) isomer was characterized in this case. For the β isomer, Melting point=190-194 C. w/decomp Calculated for C$_{24}$H$_{27}$N$_3$O$_4$S.0.20 Ethyl acetate: C, 63.21; H, 8.92; N, 5.82. Found: C, 63.06; H, 5.95; N, 8.94.

The following compounds were prepared by chemistry similar to that described for Example 8.

| Example | Structure | stereo | Salt form | MP (°C.) |
|---|---|---|---|---|
| 9 | 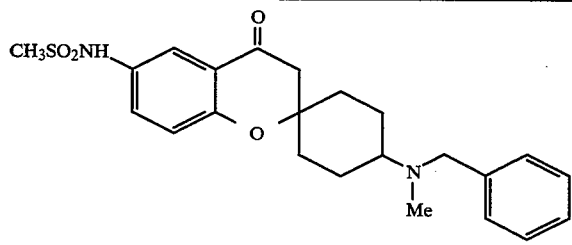 | Alpha | Free base | 192–19 |
|  |  | Beta | Free base | 186–18 |
| 10 | 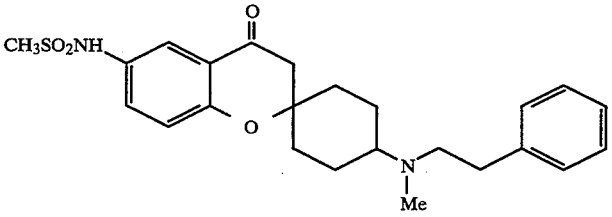 | Alpha | Free base | 176–17 |
|  |  | Beta | Free base | 169–17 |
| 11 | 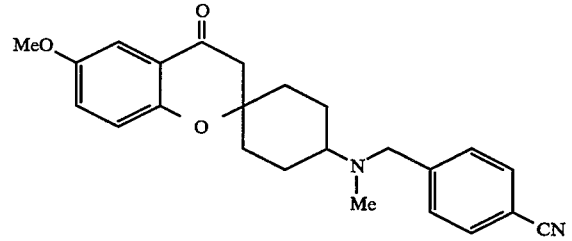 | Beta | Free base | 128–13 |
| 12 | 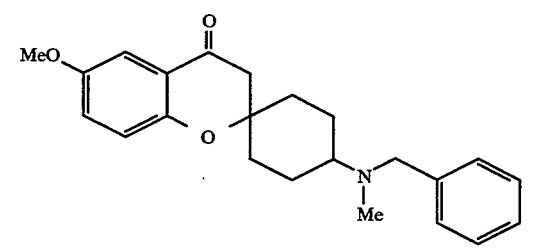 | Alpha | HCl | 224–22 |
|  |  | Beta | Free base | 110 |

| Example | Structure | stereo | Salt form | MP (°C.) |
|---|---|---|---|---|
| 13 | 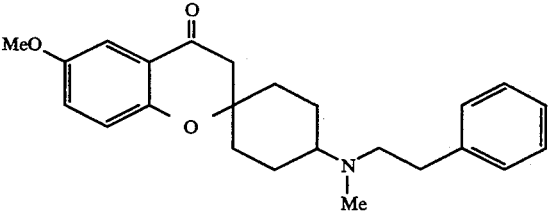 | Alpha | HCl | 225–22 |
|  |  | Beta | HCl | 206–20 |

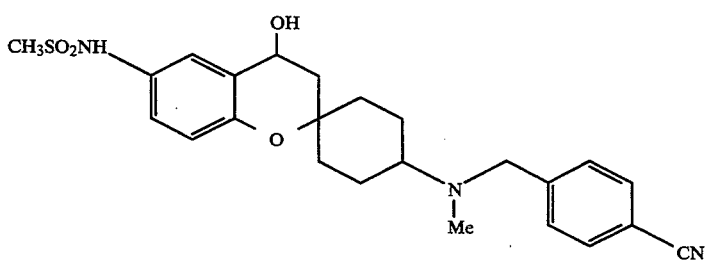

EXAMPLE 14

N-[N'-Methyl-N'(p-cyanobenzyl)-4'-amino-3,4-dihydro-4-hydroxyspiro[2H-1-benzopyran-2,1'-cyclohexan]-6-yl]methanesulfonamide Prepared from the product of example 8 (N-[N'-Methyl-N'(p-cyanobenzyl)-4'-amino-3,4-dihydro-4-oxospiro[2H-1-benzopyran-2,1'-cyclohexan]-6-yl]methanesulfonamide) by a procedure identical to that already described for the preparation of the product of Example 2

MP=225–228 Anal. Calcd. For $C_{24}H_{29}N_3O_4S$: C, 58.59; H,6.15; N, 8.54. Found: C, 58.21; H,5.99; N, 8.65.

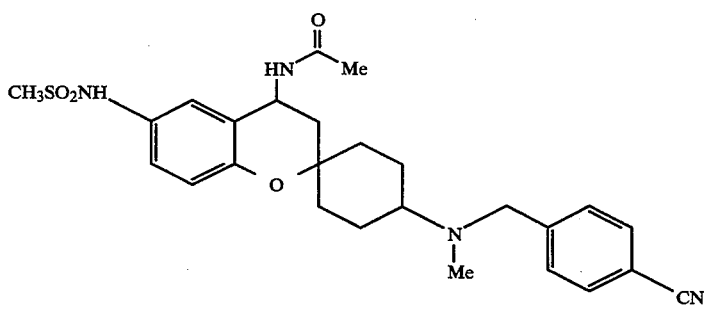

EXAMPLE 15

N-[N'-Methyl-N'(p-cyanobenzyl)-4'-amino-3,4-dihydro-4-acetamidospiro[2H-1-benzopyran-2,1'-cyclohexan]-6-yl]methanesulfonamide Prepared from the product of example 14 by a procedure identical to that already described for the preparation of the product of Example 7

MP=188–190 Anal. Calcd. For $C_{26}H_{32}N_4O_4S \cdot 0.45$ ethyl acetate: C, 62.26; H,6.69; N, 10.45. Found: C, 62.03; H,6.30; N, 10.35.

EXAMPLE 16

METHANESULFONAMIDE, N-[2'-(DIMETHYLAMINO)-1,4-DIHYDROSPIRO[3H-2-BENZOPYRAN-3'-CYCLOHEXAN]-7-YL]-,CIS-ISOMER

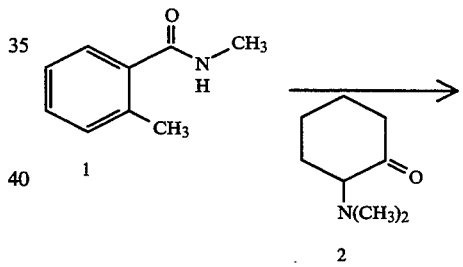

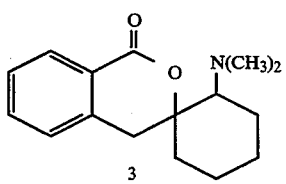

A solution of methyltoluamide 1 (8.95 grams, 60 mmol) in 240 mL of dry THF cooled to 0 ° C. was treated with n-Butyl lithium (75 mL, 120 mmol) and stirred for 30 minutes. This mixture was cooled to −70 ° C. and a solution of 2-dimethylaminocyclohexanone (2.82 grams, 20 mmol) in 3 mL of THF was added and stirred for 1.5 hrs. The reaction was warmed to 0 ° C. and quenched with saturated aqueous NaCl. After extraction with ethyl acetate, the organic portion was extracted with 2N HCl. The aqueous was washed with ethyl acetate and then basified with 40% NaOH in water. Extraction of the aqueaous with ethylacetate, drying with sodium sulfate and concentration gave a crude alcohol intermediate which was treated with 34 mL of 50% acetic acid in water followed by 8 mL of concentrated sulfuric acid. The mixture was heated at 100 ° C. for 24 hrs. This was diluted with water and extracted with ethyl acetate. The aqueous was basified with 40% NaOH and extracted with ethyl acetate. The organic portions from the basic extractions were combined dried over sodium sulfate and concentrated. Filtration of the residue through silica gel eluted with ethyl acetate, concentration and crystalization from hexane gave 2.55 grams (50%) of 3 as a white solid mp=95°–96° C.

$^1$H NMR (CDCl$_3$, partial): 4.25 (d, J=8 Hz, 1H); 8.07(d, J=8 Hz, 1H) ppm.

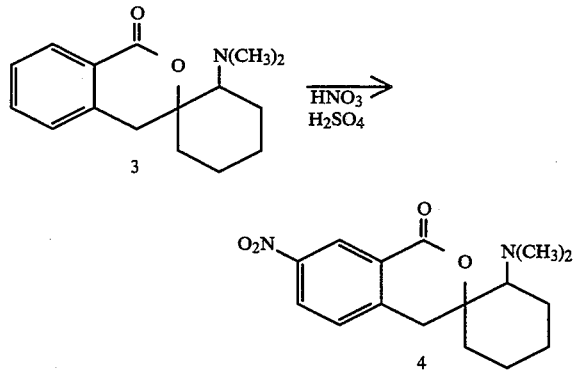

Lactone 3 (2.43 grams, 9.38 mmol) was added to 20 mL of concentrated sulfuric acid cooled to −5 ° C. and vigorously stirred while concentrated nitric acid was added dropwise (0.6 mL, 14 mmol) After the reaction was complete by HPLC analysis, the mixture was poured into ice and basified to Ph=9.5 with 40% aqueous sodium hydroxide. Extraction with methylene chloride, drying (Na$_2$SO$_4$) and concentrating gave 2.85 grams of 4 as a yellow solid (99%).

$^1$H NMR (CDCl$_3$, partial): 4.33 (d, J=7 Hz, 1H); 8.91 (d, J=2 Hz, 1H) ppm.

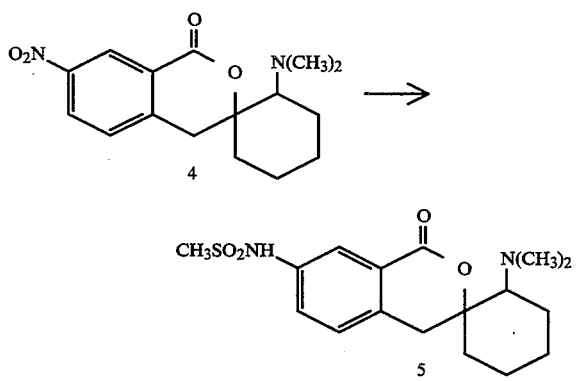

Nitro-lactone 4 (2.85 grams, 9.36 mmol) was disolved in 125 mL of 50% ethanol/THF. 3.00 grams of Raney Nickel were added and the bottle presurrized to 45 PSI with hydrogen. After shaking for 15 hrs the catalyst was removed by filtration and the solvent evaporated to give a white solid (2.50 grams, 97%). This crude aniline was disolved in 30 mL of pyridine and cooled to 0 ° C. Methansulfonyl chloride (1.06 mL, 13.7 mmol) was added and the cooling bath removed. After 2 hrs, the reaction was diluted with methylene chloride and washed with saturated aqueous sodium carbonate, dried (Na$_2$SO$_4$) and concentrated to a foam to give 3.00 grams (90%) of the free base 5.

$^1$H NMR (CDCl$_3$, partial): 4.22 (d, J=15 Hz, 1H); 7.84 (d, J=2Hz, 1H) ppm.

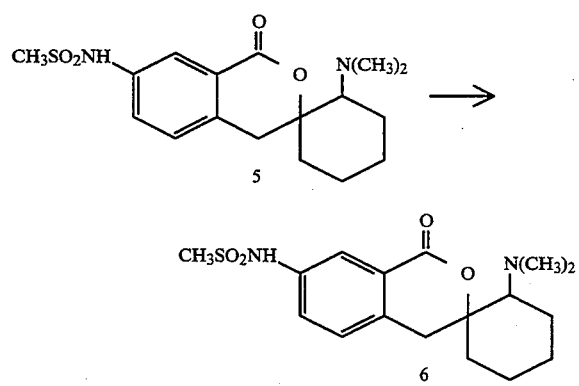

Lactone 5 (1.52 grams, 7.8 mmol) was disolved in 25 mL of THF and cooled to 0 ° C. Lithium aluminum hydride (11.7 mL of 1M solution in THF) was added dropwise. The mixture was stirred 1.5 hrs and quenched with water and filtered. The solid precipitate was collected and stirred in methanol and filtered. The filtrates were combined and concentrated to an oily solid. This crude diol was disolved in 25 mL of 85% phosphoric acid and heated for 30 minutes to 100 ° C. This was cooled, diluted with water (200 mL) and neutralized to pH=8.5 with 40% aqueous NaOH. Extraction with methylene chloride, drying (sodium sulfate), concentrating to a foam and trituration with ether/hexane gave 6 as a white solid (885 mgs, 55%) mp=167°–169° C.

$^1$H NMR (CDCl$_3$, partial): 2.10 (d, J=16 Hz, 1H); 2.33 (s, 6H); 2.98 (s, 3H) 3.80(d, J=16 Hz, 1H); 4.67 (dd, 2H) ppm.

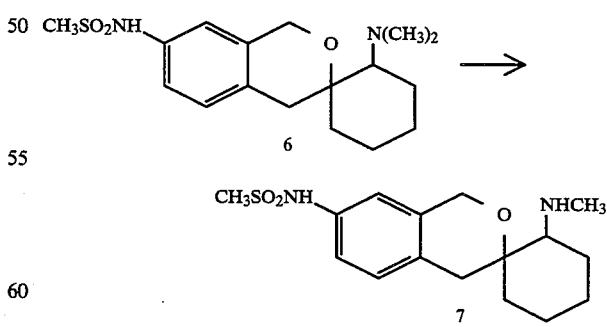

The dimethyl amine 6 (677 mgs, 2 mmol) in 6 mL of dichloroethane was cooled to 0 ° C, treated with 643 mgs (3 mmol) of proton sponge, and 1.03 mL of α-chloroethylchloroformate (4 mmol) and warmed to 80 ° C. for 8 hrs. The mixture was filtered through silicagel and eluted with ethylacetate. The solvents were removed and the residue disolved in methanol and refluxed for 22 hrs. The methanol was removed in vacuo and the residue triturated with ether. The insoluble oil was chromatographed on silicagel using 5% methanol in methylene chloride containing ammonia. Concentration of appropriate fractions gave 530 rags (80%) of 7 as an oil.

$^1$H NMR (CDCl$_3$, partial): 2.43(s, 3H); 2.90(s, 3H); 3.40 (d, 1H); 4.70 (s, 2H) ppm.

EXAMPLE 17
METHANESULFONAMIDE. N-[1,4-DIHYDRO-2'-[METHYL[2-[4-[METHYL-SULFONYL)AMINO]PHENYL]ETHYL]AMINO]-SPIRO[3H-2-BENZOPYRAN-3.1'-CYCLOHEXAN]-7-YL]-.CIS MONOHYDROCHLORIDE

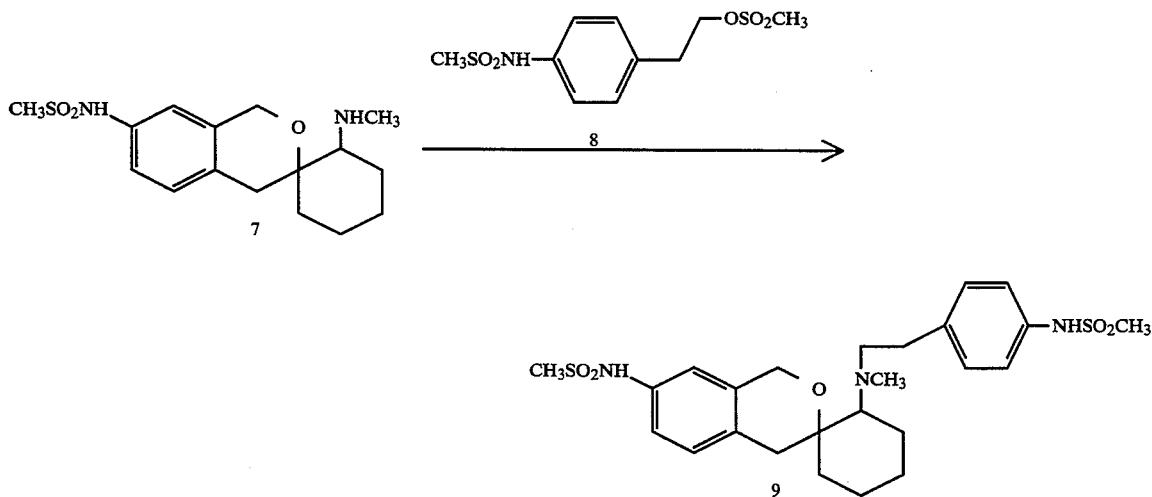

The amine 7 (100 mgs, 0.31 mmol) disolved in 0.5 mL acetonitrile was treated with methansulfonate 8 (270 mgs, 0.92 mmol ), 10 mgs of KI, and 168 mgs(2 mmol) of solid sodium bicarbonate. The mixture was heated to 80° C. for 20 hrs. The mixture was diluted with ethyl acetate and 0.5N aqueous HCl. The aqueous layer was seperated and washed with ethyl acetate. The aqueous was basified with 40% aq NaOH to pH=8.7 and extracted with dichloromethane. The organic portion was dried(sodium sulfate), concentrated to give 9 as a foam which was converted to the hydrochloride salt in ethanol usine dry HCl gas. The salt was recrystalized from hot ethanol to give 130 mgs of the amine hydrochloride 9, mp=253–255 (dec). $^1$H NMR (d6 DMSO, partial): 2.98 (s, 6H); 3.39 (s, 3H); 4.75(dd, 2H)

EXAMPLE 18
METHANESULFONAMIDE, N-[1,4-DIHYXDRO-2'-[METHYL[2-(2-PYRIDINYL)ETHYL]AMINO]SPIRO[3H-2-BENZOPYRAN-3,'-CYCLOHEXAN]-7-YL]-,CIS,-DIHYDROCHLORIDE

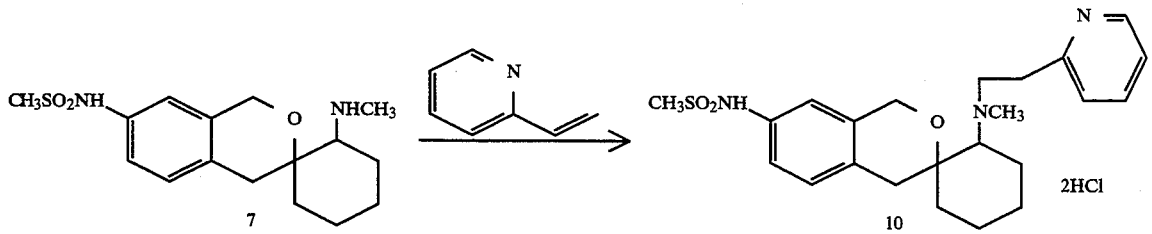

A solution of 136 mgs(0.38 mMol) amine 7 was treated with 0.7 ml of ethanol and 135 mgs sodium bicarbonate (1.5 mmol) and 0.7 ml of 2-vinylpyridine for 2 days at 25 ° C. and for 1 day at reflux. The mixture was concentrated, chromatographed (silica gel, 1% methanol, in ammonia saturated methylene chloride), and convened to the dihydrochloride in isopropanol to give 13 mgs of product mp=160°–165° C. (dec).

$^1$H NMR (d6 DMSO, partial):2.95 (s, 3H); 3.00 (s, 3H); 4.75 (q, 2H) ppm.

EXAMPLE 19
IN VITRO TEST FOR CLASS III ANTIARRHYTHMIC ACTIVITY

PURPOSE:
This in vitro assay is designed to assess possible potassium channel blocking activity of a compound based on its ability to prolong effective refractory period (ERP) in isolated papillary muscle.

TISSUE PREPARATION:
Ferrets (700 to 1200 grams) are anesthetized with 0.7 mL of a mixture of xylazine and ketamine HCL in 1:7 ratio. Papillary muscles from the right ventricle are quickly excised from the isolated heart and mounted in 50 mL organ baths containing Krebs-Henseleit solution (pH=7.2–7.4)at 37–° C. The composition of the solution in millimoles per liter are as follows: NaCl, 118; KCl, 4.7; Na$_2$CO$_3$, 23; CaCl$_2$.2H$_2$, 2; MgSO$_4$.7H$_2$O, 1.2;

$KH_2PO_4$, 1.2; Dextrose, 11.1. Timolol ($10^{-7}M$) is added to the solution to block the effects of released catecholamines during stimulation of the muscles. This solution is aerated with 95% $O_2$ and 5% $CO_2$. The tissue is stimulated at 1 Hz at one msec pulse duration by a square wave stimulator at a voltage 30% above the threshold through platinum electrodes that touch the tissue just above the bottom attachment point. The tendenous end of the tissue is connected by thread to an isometric force transducer leading to a polygraph.

EFFECTIVE REFRACTORY PERIOD (ERP) MEASUREMENT:

The ERP is determined by a standard 2 pulse protocol. Both pulses are stimulated at 1.3×voltage threshold. While pacing the tissue at a basal frequency of 1 Hz, a single extra stimulus is delivered after a variable time delay. The shortest delay resulting in a propagated response is defined as the ERP.

PROTOCOL:

1. Tissues are mounted with a resting tension of 0.5 gms, stimulated at 1 Hz, and allowed to equilibrate for 2 hours with washings at 15–20 minute intervals.
2. Voltage is adjusted to 30% above threshold and resting tension is adjusted for maximum developed reequilibration time.
3. Effective refractory period is measured at 1 Hz. Changes in resting tension and developed force are noted.
4. After equilibration, ERP's and developed force are measured at 30 minutes following the addition of increasing cumulative concentrations for test agent to the organ bath. Four to five concentrations of test agents were used to generate a concentration-response curve.
5. Four tissues per compound am tested.

RESULTS:

Employing the above protocol, it has been found that the effective concentration of most of the compounds of this invention required to increase the refractory period by an increment of 25% above baseline is less than or equal to 10 micromolar, i.e. $EC_{25}$ less than or equal to 10 micromolar, whereas sotalol in the same protocol has an $EC_{25}$ of approximately 20 micromolar.

EXAMPLE 20

PREPARATION OF INTRAVENOUS SOLUTIONS

A solution containing 0.5 mg of active ingredient per mL of injectable solution is prepared in the following manner: A mixture of 0.5 mg of active ingredient is dissolved in 1 mL of acetate buffer. The pH is adjusted using hydrochloric acid or aqueous sodium hydroxide to about pH 5.5. If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The slution is prepared and stored in such a manner that it is suitably protected from the deleterious efffects of the atmosphere. One method by which this can be accomplished is by preparation and storage of the solution in an atmosphere of nitrogen. The resulting solution is sterilized by autoclaving. Injectable solutions comprising 0.001, 0.01 and 0.1 mg, respectively, of active ingredient per mL of solution are similarly prepared substituting the indicated amount for the above-illustrated 10 mg quantity. Bulk injectable solutions of convenient volume for subsequent delivery in unit dosage form are readily prepared following the above procedure.

EXAMPLE 21

TABLET PREPARATION:

Tablets containing 1.0, 2.0, 25, 26.0, 50.0 and 100.0 mg, respectively, of active ingredient are prepared as illustrated below.

| TABLE FOR DOSES CONTAINING FROM 1-25 mg OF THE ACTIVE COMPOUND | | | |
|---|---|---|---|
| | Amount in mg | | |
| Active ingredient | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 mg OF THE ACTIVE COMPOUND | | | |
|---|---|---|---|
| | Amount in mg | | |
| Active ingredient | 26.0 | 50.0 | 100.0 |
| Microcrystalline cellulose | 25.0 | 100.0 | 200.0 |
| Modified food corn starch | 0.39 | 4.25 | 8.5 |
| Magnesium stearate | 0.39 | 0.75 | 1.50 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50 mg, and 100 mg of active ingredient per tablet.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the (general) structural formula:

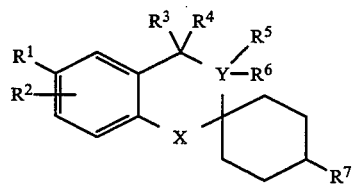

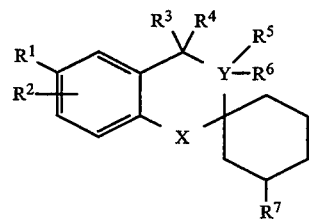

-continued

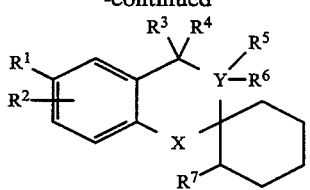

or a pharmaceutically acceptable salt, hydrate or crystal form thereof, wherein;

X is O, S, or CH₂
Y is C or O with the proviso that:
If Y=O, than R5 and R6 are nothing
If Y=O, than X=CH₂
If X=O or S, than Y=C
$R^1$ is H₃CSO₂NH—, H₃CO—, $C_{1-6}$AlkylSO₂—, $C_{1-6}$AlkylCONH— or NO₂—;
$R^2$ is —H, —OCH₃ or $C_{1-6}$Alkyl;
$R^3$ and $R^4$ taken together are=O, or $R^3$ is H and $R^4$ is one of the following —OH, —NHCOCH₃, —NHCOCH₃SO₂Phenyl, —NHCOCH₃SO₂ $C_{1-6}$Alkyl, NHCOCH₂SPhenyl, NHCOCH₂S $C_{1-6}$Alkyl, —NHCOC(CH₃)₂OH or NHSO₂ $C_{1-6}$Alkyl; or R3=R4=H
$R^5$ and $R^6$ are independently H, C1–C6 Alkyl(, or when taken together are —(CH₂)$_n$—, where n=2–5); or =CH₂;
$R^7$ is selected from

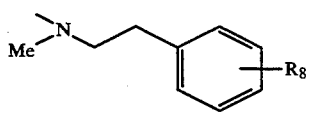

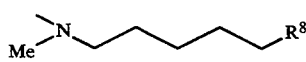

And R8 is H, —CH₃, —OH, —CN, —O—C1–C6-alkyl, —NHCO $C_{1-6}$Alkyl, —NHSO₂ $C_{1-6}$Alkyl, —SO₂ $C_{1-6}$Alkyl are Class III antiarrhythmic agents.

2. Compounds of the (general) structural formula:

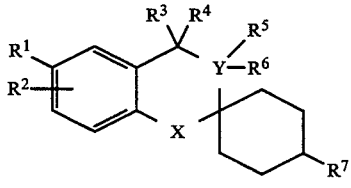

-continued

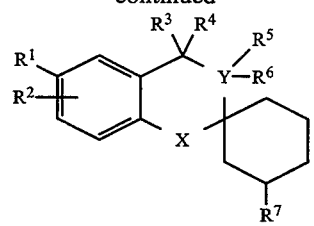

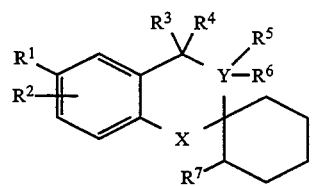

or a pharmaceutically acceptable salt, hydrate or crystal form thereof, wherein;

X is O, S, or CH₂
Y is C or O with the proviso that:
If Y=O, than R5 and R6 are nothing
If Y=O, than X=CH₂
If X=O or S, than Y=C
$R^1$ is H₃CSO₂NH—, H₃CO—, $C_{1-6}$AlkylSO₂—, $C_{1-6}$AlkylCONH— or NO₂—;
$R^2$ is —H, —OCH₃ or $C_{1-6}$Alkyl;
$R^3$ and $R^4$ taken together are=O, or $R^3$ is H and $R^4$ is one of the following —OH, —NHCOCH₃, —NHCOCH₃SO₂Phenyl, —NHCOCH₃SO₂ $C_{1-6}$Alkyl, NHCOCH₂SPhenyl, NHCOCH₂S $C_{1-6}$Alkyl, —NHCOC(CH₃)₂OH or NHSO₂ $C_{1-6}$Alkyl; or R3=R4=H
$R^5$ and $R^6$ are independently H, C1–C6 Alkyl(, or when taken together are —(CH₂)$_n$—,where n=2–5); or =CH₂;
$R^7$ is selected from

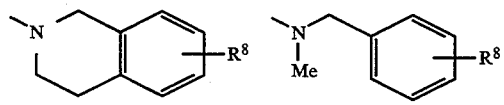

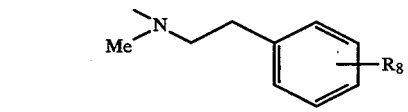

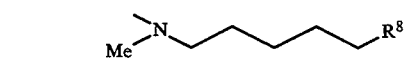

And R8 is H, —CH₃, —OH, —CN, —O—C1–C6-alkly, —NHCO $C_{1-6}$Alkyl, —NHSO₂ $C_{1-6}$Alkyl, —SO₂ $C_{1-6}$Alkyl are class III antiarrhythmic agents.

3. A compound selected from the group consisting of N-[4′-(3,4-dihydro-2 (1H)-isoquinolinyl)-3,4-dihydro-4-oxospiro[2H-1-benzopyran-2,1′-cyclohexan]-6-yl]methanesulfonamide alpha and beta isomers N-[4′-(3,4-dihydro-2(1H)-isoquinolinyl)-3,4-dihydro-4-oxospiro[2H-1-benzopyran-2,1′-cyclohexan]-6-yl]methanesulfonoamide alpha and beta isomers

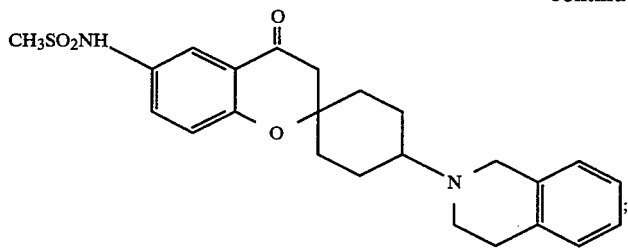

N-[4'-(3,4-dihydro-2(1H)-isoquinolinyl)-3,4-dihydro-4-hydroxyspiro[2H-1-benzopyran-2,1'-cyclohexan]-6-yl]methanesulfonamide alpha and beta isomers

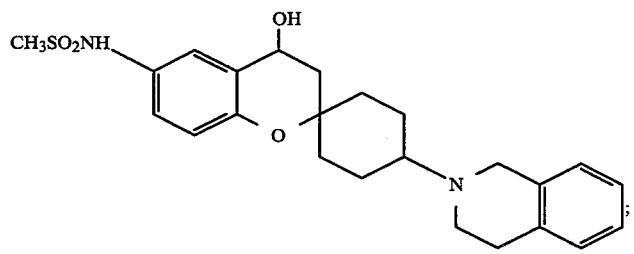

N-[4'-(3,4-dihydro-2(1H)-isoquinolinyl)-3,4-dihydrospiro[2H-1-benzopyran-2,1'-cyclohexan]-6-yl]methanesulfonamide beta isomer

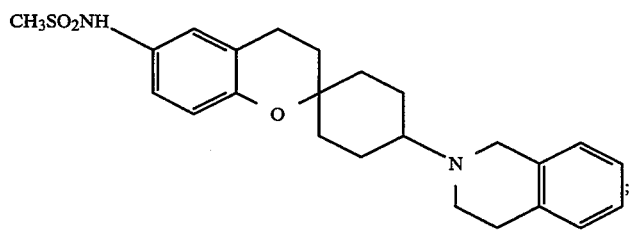

N-[4'-(3,4-dihydro-2(1H)-isoquinolinyl)-3-methyl-3,4-dihydrospiro[2H-1-benzopyran-2,1'-cyclohexan]-6-yl]methanesulfonamide alpha and beta isomers

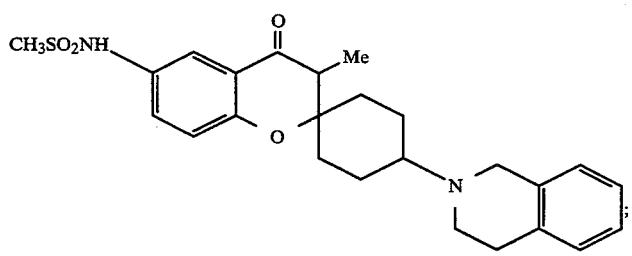

N-[4'-(6-cyano-3,4-dihydro-2(1H)-isoquinolinyl)-3,4-dihydro-4-oxospiro[2H-1-benzopyran-2,1'-cyclohexan]-6-yl]methanesulfonamide alpha and beta isomers

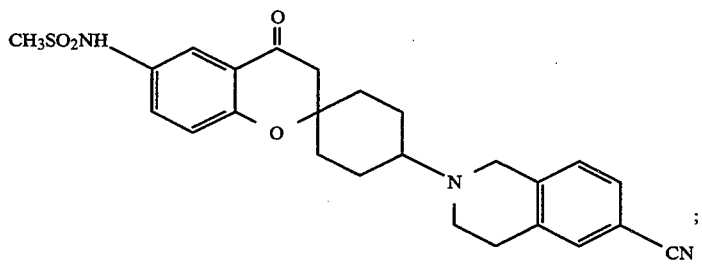

N-[4'-(6-cyano-3,4-dihydro-2(1H)-isoquinolinyl)-3,4-dihydro-4-hydroxyspiro[2H-1-benzopyran-2,1'-cyclohexan]-6-yl]methansulfonamide beta isomer

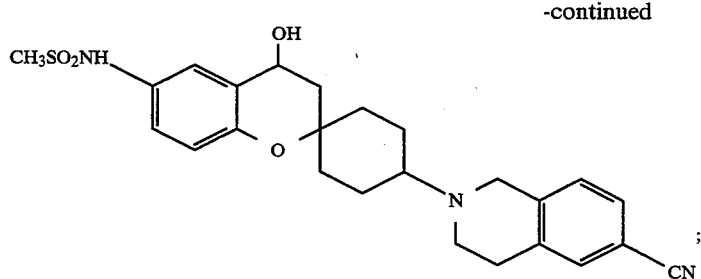

N-[4'-(3,4-dihydro-2(1H)-isoquinolinyl)-3,4-dihydro-4-acetamidospiro[2H-1-benzopyran-2,1'-cyclohexan]-6-yl]methansulfonamide beta isomer

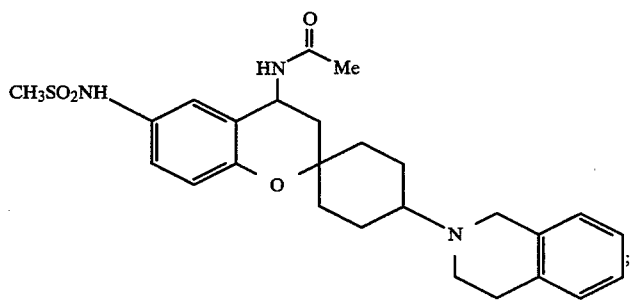

N-[N'-Methyl-N'(p-cyanobenzyl)-4'-amino-3,4-dihydro-4-oxospiro[2H-1-benzopyran-2,1'cyclohexan]-6-yl]methanesulfonamide alpha and beta isomers

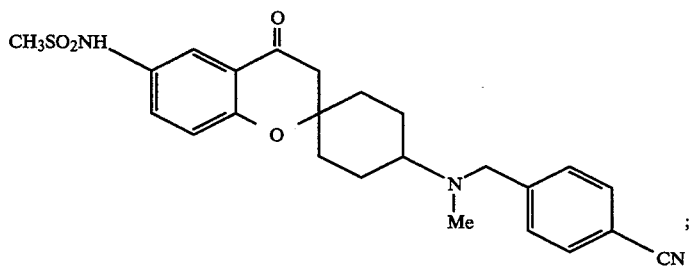

N'-Methyl-N'-benzyl-4'-amino-3,4-dihydro-4-oxospiro[2H-1-benzopyran-2,1'-cyclohexan]-6-yl]methanesulfonamide alpha and beta isomers

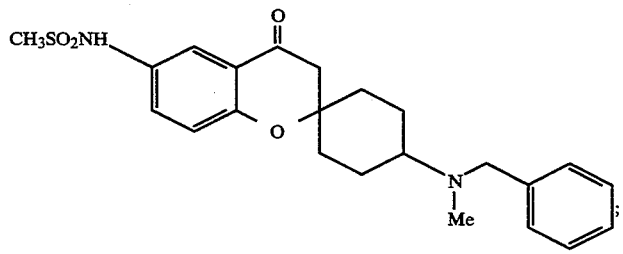

N'-Methyl-N'-phenethyl-4'-amino-3,4-dihydro-4-oxospiro-[2H-2-benzopyran-2,1'-cyclohexan]-6-yl]methanesulfonamide alpha and beta isomers

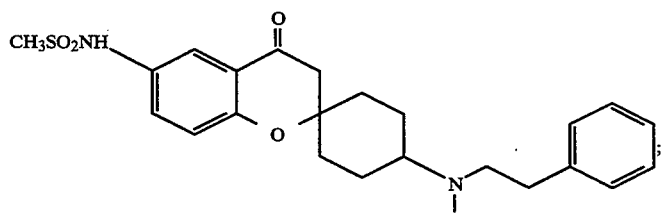

N'-Methyl-N'-p-cyanobenzyl-4'-amino-3,4-dihydro-6- methoxy-4-oxospiro[2H-1-benzopyran-2,1'-cyclohexane beta isomer

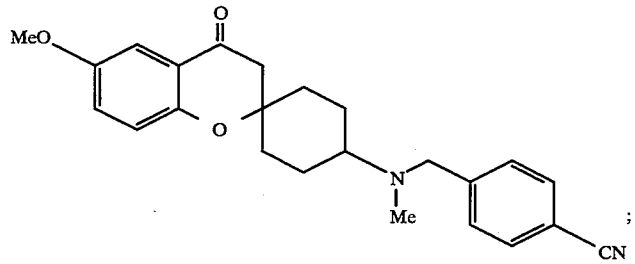

N'-Methyl-N'-benzyl-4'-amino-3,4-dihydro-6-methoxy-4-oxospiro[2H-1-benzopyran-2,1'-cyclohexane alpha and beta isomers

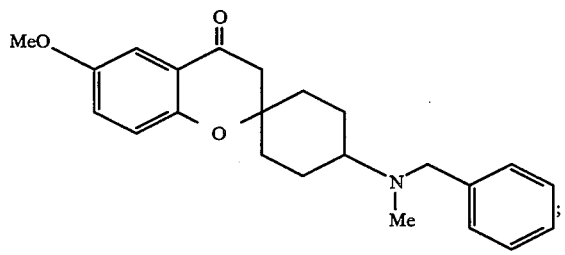

N'Methyl-N'-phenethyl-4'-amino-3,4-dihydro-6-methoxy-4-oxospiro[2H-1-benzopyran-2,1'-cyclohexane alpha and beta isomers

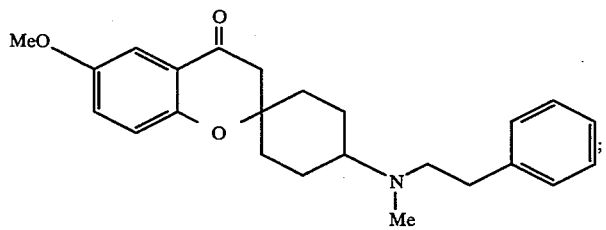

N-[N'-Methyl-N'(p-cyanobenzyl)-4'-amino-3,4-dihydro-4-hydroxyspiro[2H-1-benzopyran-2,1'-cyclohexan]-6-yl]methanesulfonamide beta isomer

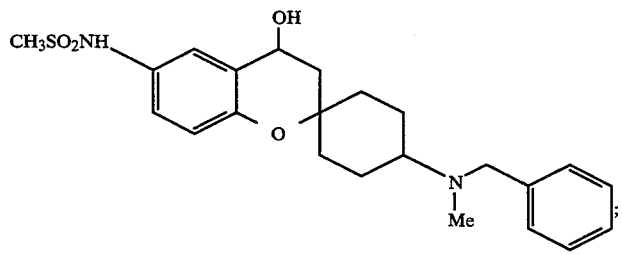

N-[N'-Methyl-N'(p-cyanobenzyl)-4'-amino-3,4-dihydro-4-acetamidospiro[2H-1-benzopyran-2,1'-cyclohexan]-6-yl]methanesulfonamide beta isomer

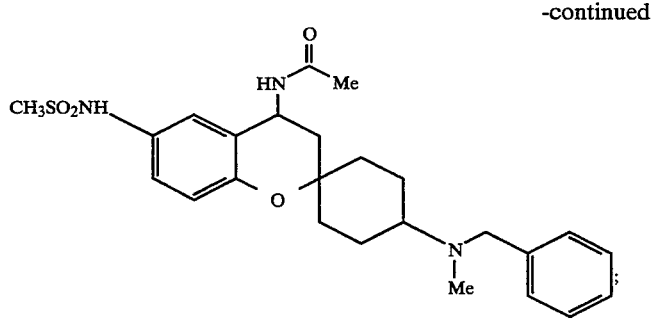

or pharmaceutically acceptable salts, hydrates and crystal forms thereof.

4. A pharmaceutical formulation for use in the treatment of arrhythmia comprising a carrier and (a therapeutically effective amount of a) an amount of a compound of claim 1 such that a dosage form prepared from the formulation contains from 1 to 100 mg of the compound.

5. The pharmaceutical formulation of claim 4, comprising, in addition, a pharmaceutically effective amount of one or more of a Class I, Class II or Class IV antiarrhythmic agent.

6. The pharmaceutical formulation of claim 4, wherein the pharmaceutically effective amount of compound ranges from about 0.0001 to about 20 mg per kg of body weight per day.

7. The pharmaceutical formulation of claim 4, wherein the pharmaceutically effective amount of compound ranges from about 0.001 to about 10 mg per kg of body weight per day.

8. A method of treating arrhythmia and/or impaired cardiac pump function in a patient in need of such treatment which comprises administering to such patient a therapeutically effective amount of the comound of claim 1.

9. The method of claim 7, comprising, in addition, the admnistration of one or more of a Class I, Class II or Class IV antiarrhythmic agent.

10. The method of claim 7 wherein the therapeutically effective amount of compound is administered orally, intraperitoneally, subcutaneously, intramuscularly, transdermally, sublingually or intravenously.

11. The method of claim 7 wherein the therapeutically effective amount of comound is administered orally or intravenously.

* * * * *

UNITED STATES PATENT AND TRADEMARK OFFICE
CERTIFICATE OF CORRECTION

PATENT NO. : 5,403,846
DATED : Apr. 4, 1995
INVENTOR(S) : John J. Baldwin, et al It is certified that error appears in the above-indentified patent and that said Letters Patent is hereby corrected as shown below:

In Claim 2, column 34, line 55 should read:

alkyl, -NHCO $C_{1-6}$Alkyl, -NHSO$_2$ $C_{1-6}$Alkyl,

In Claim 3, column 34, please delete all text after line 62 to the bottom of the page.

In Claim 3, column 39, at approximately line 34 (line numbers were omitted), line should read:

N'-Methyl-N'-phenethyl-4'-amino-3,4-dihydro-6-methoxy-4-

Signed and Sealed this

Fifth Day of December, 1995

Attest:

BRUCE LEHMAN

Attesting Officer

Commissioner of Patents and Trademarks